US008629135B2

(12) United States Patent
Gujral et al.

(10) Patent No.: US 8,629,135 B2
(45) Date of Patent: Jan. 14, 2014

(54) PHARMACEUTICAL COMPOSITIONS COMPRISING RET INHIBITORS AND METHODS FOR THE TREATMENT OF CANCER

(75) Inventors: Taranjit S. Gujral, Cambridge, MA (US); Lois M. Mulligan, Kingston (CA); Vinay K. Singh, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 23 days.

(21) Appl. No.: 13/003,218

(22) PCT Filed: Jul. 14, 2009

(86) PCT No.: PCT/CA2009/000994
§ 371 (c)(1),
(2), (4) Date: May 2, 2011

(87) PCT Pub. No.: WO2010/006432
PCT Pub. Date: Jan. 21, 2010

(65) Prior Publication Data
US 2011/0201598 A1 Aug. 18, 2011

Related U.S. Application Data

(60) Provisional application No. 61/129,695, filed on Jul. 14, 2008.

(51) Int. Cl.
| *A01N 43/00* | (2006.01) |
| *A61K 31/55* | (2006.01) |
| *A01N 33/02* | (2006.01) |
| *C07C 209/00* | (2006.01) |
| *C07C 215/00* | (2006.01) |
| *C12N 9/99* | (2006.01) |
| *C07D 313/00* | (2006.01) |

(52) U.S. Cl.
USPC ........... 514/217; 514/654; 514/651; 514/655; 514/643; 564/380; 564/352; 564/387; 435/184; 549/354

(58) Field of Classification Search
USPC .......... 514/217, 651, 510, 655, 643; 564/380, 564/352, 387; 435/184; 549/354
See application file for complete search history.

(56) References Cited

U.S. PATENT DOCUMENTS

| 3,978,121 | A | 8/1976 | Engelhardt |
| 4,771,056 | A | 9/1988 | Rozencwaig |
| 6,395,788 | B1 | 5/2002 | Iglehart, III |
| 7,411,072 | B2 | 8/2008 | Coghlan et al. |
| 2003/0099711 | A1 | 5/2003 | Meadows et al. |
| 2004/0072824 | A1 | 4/2004 | Telerman et al. |

FOREIGN PATENT DOCUMENTS

| EP | 2036557 | 3/2009 |
| WO | 02/18368 | 3/2002 |
| WO | 02/43652 | 6/2002 |
| WO | 03070249 | 8/2003 |
| WO | 03/072549 | 9/2003 |
| WO | 2006014420 | 2/2006 |
| WO | 2006023757 | 3/2006 |
| WO | 2008098351 | 8/2008 |
| WO | 2009055001 | 4/2009 |
| WO | 2009018088 | 5/2009 |
| WO | 2009/088838 | 7/2009 |
| WO | 2009/148623 | 12/2009 |

OTHER PUBLICATIONS

BC Cancer Agency Cancer Drug Manual (1994) 8 pgs.*
DeBonis S., et al., "In vitro screening for inhibitors of human mitotic kinesin Eg5 with antimitotic and antitumor activities," Molecular Cancer Therapeutics. vol. 3, No. 9: 217-227 (2004).
Kodama, Y. et al., "The RET proto-oncogene: A molecular therapeutic target in thyroid cancer" Cancer Science, vol. 96, No. 3: 143-148 (2005).
Gujral, T. et al., "Molecular mechanisms of RET receptor-mediated oncogenesis in multiple endocrine neoplasia 2B," Cancer Research, vol. 66, No. 22: 10741-10749 (2006).
Gujral, T. et al., "A novel RET kinase-B-catenin signaling pathway contributes to tumorigenesis in thyroid carcinoma" Cancer Research, vol. 68, No. 5: 1338-1346 (2008).
Santarpia et al., "Beyond RET: potential therapeutic approaches for advanced and metastatic medullary thyroid carinoma" Journal of Internal Medicine, vol. 266, No. 1: 99-113 (2009).
Lanzi et al., "Targeting RET for thyroid cancer therapy" Biochemical Pharmacology vol. 77, No. 3: 297-309 (2009).
PCT International Search Report for International Patent Application No. PCT/CA2009/000994 dated Oct. 28, 2009.
PCT Written Opinion of the International Searching Authority for International Patent Application No. PCT/CA2009/000994 dated Oct. 28, 2009.
PCT International Preliminary Report on Patentability for International Patent Application No. PCT/CA2009/000994 dated Oct. 8, 2010.
Extended European Search Report for 09797316.8 dated Mar. 6, 2012.
Gujral, Taranjit S., et al., "Identification and Characterization of a Novel RET Kinase Inhibitor, SW-01", Proceedings of the American Association for Cancer Research Annual Meeting, vol. 49, Apr. 2008, p. 1161 (Abstract).
Mao, et al., Blood, "A chemical biology screen identifies glucocorticoids that regulate c-maf expression by increasing its proteasomal degradation through up-regulation of ubiquitin" 110(12), 2007, 4047-4054, Sep. 11, 2007.
Promega Dual-Glo Luciferase Assay System Technical Manual, Promega Corporation, Jun. 2006 revisions.

* cited by examiner

*Primary Examiner* — Shirley V Gembeh
(74) *Attorney, Agent, or Firm* — Lowenstein Sandler LLP; Angela Lyon; Carol Miernicki Steeg

(57) ABSTRACT

A class of compounds useful in pharmaceutical compositions and methods for treating or preventing cancer is described. The compounds' ability to inhibit RET kinase is quantified, i.e., their respective RET IC50 and EC50 values are described. One such compound, known as cyclobenzaprine and herein as SW-01, has been identified as RET-specific with an IC50 of 300 nM. SW-01 inhibits RET autophosphorylation and blocks the growth and transformation of thyroid cancer cell lines. It has been further tested in pancreatic cancer, breast cancer, and SCLC cell lines. The compounds show utility for inhibition of survival and proliferation of tumor cells.

39 Claims, 15 Drawing Sheets

PHARMACEUTICAL COMPOSITIONS COMPRISING RET INHIBITORS AND METHODS FOR THE TREATMENT OF CANCER

FIELD OF THE INVENTION

This invention is in the field of pharmaceuticals, and relates to compounds and compositions for treating/mitigating cancer, for suppressing tumour growth, and for reducing metastasis of tumour cells. More specifically, the invention is in the field of compounds and compositions for treatment of cancers including but not limited to pancreatic cancer, thyroid cancer, metastatic melanoma, breast cancer, testicular cancer, prostate cancer, colon carcinoma, and ovarian cancer.

BACKGROUND OF THE INVENTION

Cancer

Cancer affects millions of adults and children worldwide, and according to the Cancer Statistics 2006 published by the American Cancer Society, is the second leading cause of mortality in the United States today. It is a disease characterized by disorderly division of cells, combined with the malignant behaviour of these cells. Cancer therapy typically involves surgery, chemotherapy and/or radiation treatment. All of these approaches pose significant drawbacks for patients. Surgery, for example, can pose a significant risk to patient health, may not be possible due to tumour location or size, or may otherwise be unacceptable to the patient. Additionally, surgery might not completely remove neoplastic tissue. Radiation therapy has serious side effects. Traditional chemotherapy has many drawbacks since almost all known chemotherapeutic agents are toxic. Accordingly, chemotherapy can cause significant and sometimes dangerous side effects, including severe nausea, bone marrow depression, and/or immunosuppression. Additionally, many tumour cells are resistant, or develop resistance, to chemotherapeutic agents through multi-drug resistance, or development of resistance mutations.

In 2007 in the United States, there were approximately 33,550 new patients diagnosed with thyroid cancer; and an estimated 178,480 women were diagnosed with breast cancer. Pancreatic cancer is the fourth leading cause of cancer death in North America. Surgery and existing chemotherapy are generally palliative; 75% of patients with pancreatic cancer have less than 6 months to live. For this majority of patients, surgery and chemotherapy are not even offered. At this time, patients with pancreatic cancer have a 5 year survival rate of less than 3%. Surgery is currently the only treatment option for both sporadic and hereditary medullary thyroid carcinoma; radiation therapy and chemotherapy are not effective treatments (see Quayle, F. J. et al., *J. Surg. Oncol.* (2005) 89: 122-129). Small cell lung carcinoma (SCLC) and non-small cell lung carcinoma (NSCLC) are leading causes of cancer death in North America in both men and women, with expected survival rates for 5 years of 15%.

For the above reasons, there is a need for novel compounds and pharmaceutical compositions, and methods that are useful for treating cancer with either improved effect or reduced side effects or both.

SUMMARY OF THE INVENTION

It is an object of the present invention to provide compounds for the treatment and mitigation of cancer, as well as related pharmaceutical compositions.

An aspect of the present invention is a composition comprising a RET inhibitor, in an amount effective to produce a therapeutic effect. Compositions of the present invention provide useful therapeutic agents for prevention of cancer spread and/or mitigation of cancer.

Compounds of the invention show utility for inhibition of survival, proliferation and migration of tumour cells. The invention relates to compounds and compositions for treating/mitigating cancer, for suppressing tumour growth, and for reducing metastasis of tumour cells.

In an aspect, the invention provides a pharmaceutical composition for the treatment and/or mitigation of cancer, comprising an effective amount of a compound of Formula (1A):

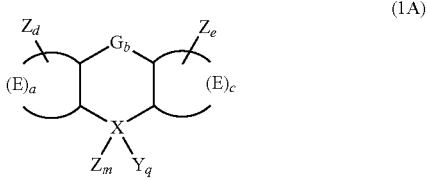

where G is S, O, NH, $CH_2$, $CH=CH$, $CR^1R^2$—$CR^1R^2$, $CR^1=CR^2$, $N=CH$, $N=N$, $O—CH_2$, $CH_2—CH_2$, $O—O$, $S—CH_2$, $S—S$, or

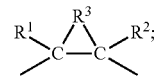

$R^1$ and $R^2$ are independently H, alkyl, or halo; $R^3$ is $CH_2$, $CR^1R^2$, S, or $NR^4$; X is $sp^2$ hybridized carbon, $sp^3$ hybridized carbon, or $sp^3$ hybridized nitrogen; Y is $sp^2$ hybridized nitrogen, $sp^3$ hybridized nitrogen, sp hybridized carbon, $sp^2$ hybridized carbon, $sp^3$ hybridized carbon, amino, $NR^4R^5$, O, S, P, ester, amide, keto, hydroxyl, $N^+R^6R^7O^-$, substituted or unsubstituted aryl, halo, nitro, carboxyl, substituted alkyl (such as, for example, aminoalkyl, halogenated alkyl), unsubstituted alkyl, or a combination thereof; $R^4$ and $R^5$ are independently H or alkyl; $R^6$ and $R^7$ are independently alkyl; E is independently $sp^2$ hybridized carbon, $sp^2$ hybridized nitrogen, $sp^3$ hybridized carbon, or $sp^3$ hybridized nitrogen, and forms a saturated or unsaturated fused ring system optionally with a heteroatom as a ring atom; Z is independently H, aryl, halo, nitro, hydroxyl, amino, thiol, alkoxyl, amido, amide, carboxyl, alkenyl, allyl, cyano, substituted alkyl (such as, for example, alkylamino, halogenated alkyl), or unsubstituted alkyl; a is 0-5; b is 0-1; c is 0-5; d is 0-7; e is 0-7; m is 0-1; and q is 1-2. In embodiments of the first aspect the compound inhibits RET kinase and the cancer is a RET-associated cancer.

An embodiment of this aspect of the invention provides a pharmaceutical composition for the treatment and/or mitigation of cancer, comprising an effective amount of a compound of Formula (1B):

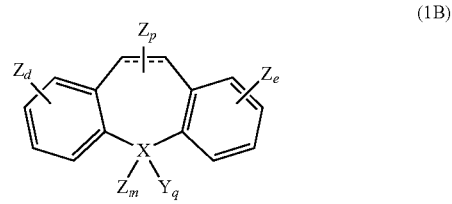

where X, Z, Y, m, d, e, and q are as defined in Formula (1A), p is 0-2, and the dotted line indicates that the compounds may be saturated or unsaturated at this location.

Another embodiment of this aspect of the invention provides a pharmaceutical composition for the treatment and/or mitigation of cancer, comprising an effective amount of a compound of Formula (1C):

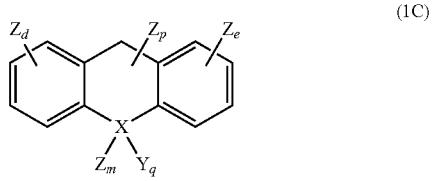

where X, Z, Y, m, d, e, p and q are as defined for Formula (1B).

An embodiment of the invention is a pharmaceutical composition with a compound of Formula (1A), (1B), or (1C), wherein Y comprises a secondary or tertiary amine. Another embodiment of the invention is a pharmaceutical composition with a compound of Formula (1A), (1B), or (1C), wherein Y comprises an $sp^2$ carbon. In certain embodiments, the central ring of the compound is unsaturated. In other embodiments, the compound is SW-01; SW-05; SW-04; SW-13; SW-12; SW-08; SW-02; SW-03; SW-15; or pharmaceutically acceptable salts thereof. In some embodiments, G is CH=CH. Certain pharmaceutical compositions further comprise a pharmaceutically acceptable vehicle. In some embodiments, the compositions are effective against medullary thyroid carcinoma as seen in multiple endocrine neoplasia type 2 (MEN 2), metastatic breast cancer, testicular cancer, small cell lung carcinoma, non-small cell lung carcinoma, or pancreatic cancer. In certain embodiments, compounds Formula (1A), (1B), or (1C) inhibit RET kinase activity.

An embodiment of the invention provides a pharmaceutical composition with a compound of Formula (1A), (1B), or (1C), further comprising one or more additional compounds which is an antineoplastic agent.

Another aspect of the invention provides a pharmaceutical composition for suppressing RET-associated tumour growth, proliferation, or both, comprising a pharmaceutical composition with a compound of Formula (1A), (1B), or (1C), and a pharmaceutically acceptable vehicle. In some embodiments of the previous aspects, the pharmaceutical composition further comprises one or more additional compounds which is an antineoplastic agent. In certain embodiments such RET-associated tumour growth or proliferation is associated with a mutation of the RET gene. In some embodiments the mutation is a change of expression of RET. In certain embodiments, the mutation is a chromosomal translocation. In some embodiments, the mutation changes affinity of RET for ATP relative to wild type RET. In certain embodiments, the mutation is an activating mutation such as a point mutation. In certain embodiments the mutation confers resistance to one or more of PP1, PP2, and vandetanib. In some embodiments the mutation is V804M or M918T.

Another aspect of the invention provides a method of treating and/or mitigating cancer, comprising administering a pharmaceutical composition including a compound of Formula (1A), (1B), or (1C) to a subject in need thereof. In embodiments of this aspect, the cancer is a RET-associated cancer.

A further aspect of the invention provides a method of suppressing RET-associated tumour growth, comprising administering a pharmaceutical composition including a compound of Formulas (1A), (1B), or (1C), to a subject in need thereof.

An aspect of the invention provides a method of inhibiting RET comprising contacting RET with a compound of Formula (1A), (1B), or (1C). The contacting may be in solution, in cell culture, or in a subject.

In embodiments of these methods the RET-associated cancer is medullary thyroid carcinoma, papillary thyroid carcinoma, pheochromocytoma, metastatic breast cancer, other multiple endocrine neoplasia type 2 related tumor, testicular cancer, small cell lung carcinoma, non-small cell lung carcinoma, or pancreatic cancer. In some embodiments, the compound of Formula (1A) inhibits RET kinase. In certain embodiments of the compound of Formula (1A), G is CH=CH. In some embodiments, X and Y are each $sp^2$ hybridized carbon. In certain embodiments, Y is bonded to a non-cyclic aliphatic group optionally comprising one or more heteroatoms. In some embodiments, d and e are each 0. In an embodiment the compound of Formula (1A) is cyclobenzaprine (SW-01).

An aspect of the invention provides a method of suppressing RET-associated tumour growth, proliferation, or both, comprising administering a pharmaceutical composition with a compound of Formula (1A), (1B), or (1C) as described above, to a subject in need thereof. In some embodiments of the invention, RET-associated tumour growth or proliferation is associated with a mutation of the RET gene. In other embodiments, the mutation is a change of expression of RET. In certain embodiments, the mutation is a chromosomal translocation. In some embodiments, the mutation changes affinity of RET for ATP relative to wild type RET. In some embodiments, the mutation is an activating mutation. In certain embodiments, the mutation is a point mutation. In some embodiments, the mutation confers resistance to one or more of PP1, PP2, and vandetanib. In certain embodiments of the invention, the mutation is V804M or M918T.

BRIEF DESCRIPTION OF THE DRAWINGS AND TABLES

Further details of the invention will become apparent from the following description, taken in combination with the appended figures and tables wherein:

FIG. 1 is a ribbon diagram showing residues 709-988 of wildtype RET's intracellular domain that represents its active conformation.

FIG. 2A is an image of a Western blot assay indicating significant RET inhibition by SW-01 in HEK293 cells expressing RET in the presence of GDNF. Presented lanes are control (no treatment, CTL), vehicle (dimethylsulfoxide, DMSO), NSC1077, NSC27476, and NSC78206 (also known as Flexeril™, cyclobenzaprine, in certain literature it is known as "MK-130", and is referred to herein as "SW-01"). Autokinase activity of RET was measured using anti-phosphoRET antibody pY905. Blots were reprobed with a pan RET antibody to detect RET protein amount.

FIG. 2B is an image of a Western blot assay demonstrating phosphorylation of purified recombinant RET in the presence or absence of increasing concentrations of SW-01. This image indicates that SW-01 significantly inhibited RET in a kinase assay using purified recombinant protein. Autokinase activity of RET was measured using anti-phosphoRET antibody pY905. Blots were reprobed with a pan RET antibody to detect RET protein amount.

FIG. 2C is an image of a Western blot assay demonstrating that SW-01 blocked RET activation by GDNF in HEK293 cells that stably express RET. Briefly, HEK293 cells were treated with DMSO vehicle only (control, indicated by [SW-01]=0) or increasing concentrations of SW-01, harvested, and subjected to Western blotting. Whole cell lysates were immunoblotted with anti-phosphoRET antibody pY905 to measure RET phosphorylation, demonstrating the degree of RET inhibition. The same blot was re-probed with a pan RET antibody to measure the amount of RET protein.

FIG. 2D is an image of a Western blot assay indicating that SW-01 blocks RET-mediated activation of ERK, as measured by phosphorylation, without affecting its protein expression levels. Whole cell lysates from GDNF treated HEK293 cells, treated with vehicle control (DMSO [−]) or increasing concentrations of SW-01, were separated by SDS-PAGE and immunoblotted with antibodies against total RET, total ERK and pERK as indicated. The amount of pERK was drastically reduced in a dose dependent fashion with increased concentration of SW-01 while the amounts of total RET and ERK proteins remained the same.

Figure 4:
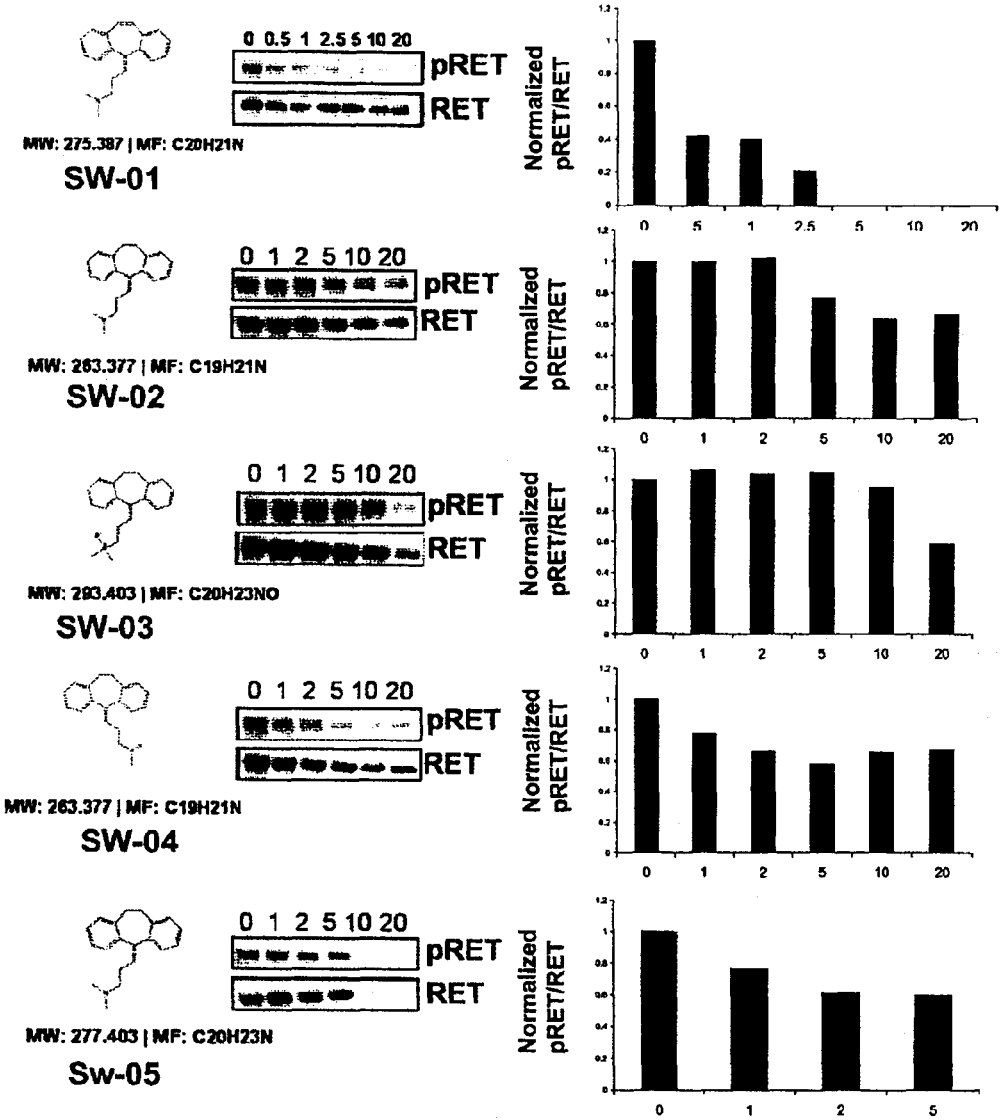

FIG. 4 is a depiction of the effects of various compounds on RET activation. Chemical structures of SW-01 and four structurally related compounds are shown. Also shown are images of Western blots showing RET phosphorylation in the presence or absence of increasing (μM) concentrations of indicated compounds, and bar graphs showing the phosphoRET/RET ratios at the specified concentration of particular test compounds.

Figure 5A:
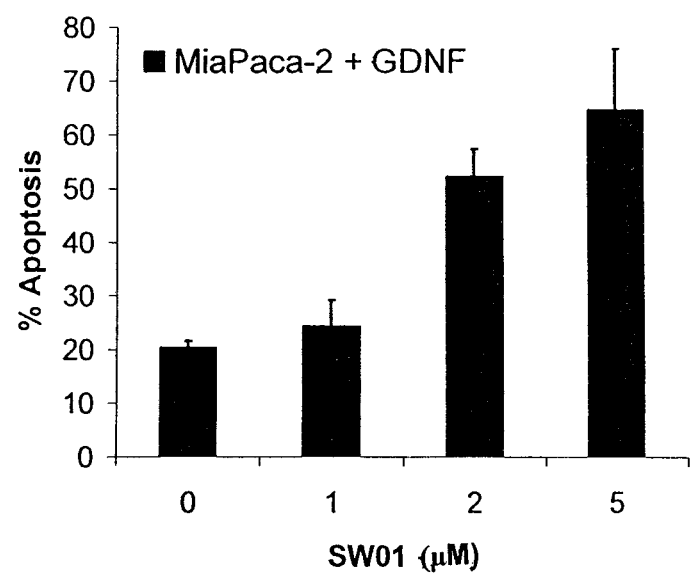

FIG. 5A is a bar graph of percentage apoptosis detected by flow cytometry versus concentration of SW-01 in a pancreatic cancer cell line (MiaPaca-2) in the presence of GDNF.

Figure 5B:
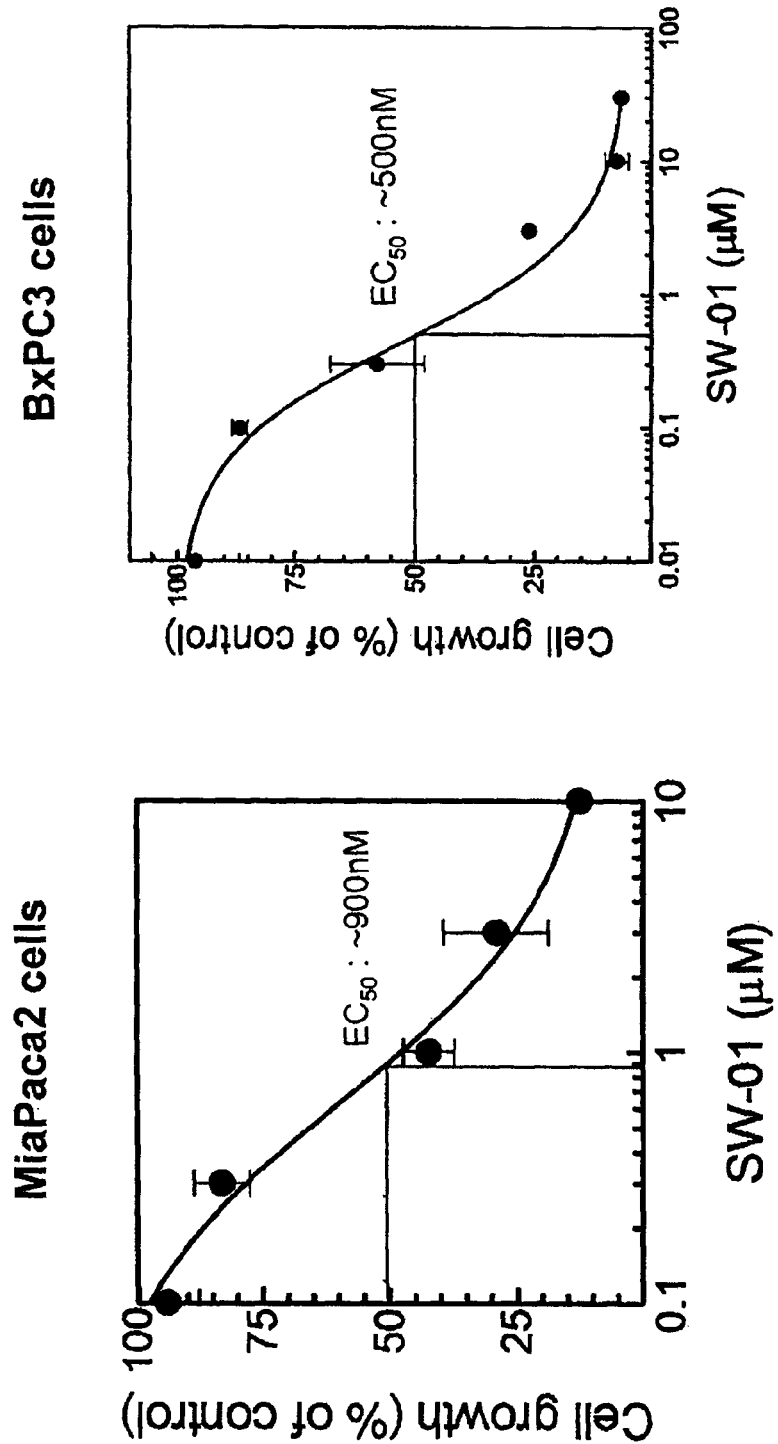

FIG. 5B is inhibition curves showing percentage cell growth relative to control detected by MTT cell proliferation assay versus increasing concentration of SW-01 in pancreatic cancer cell lines (MiaPaca-2 and BxPc3).

Figure 5C:
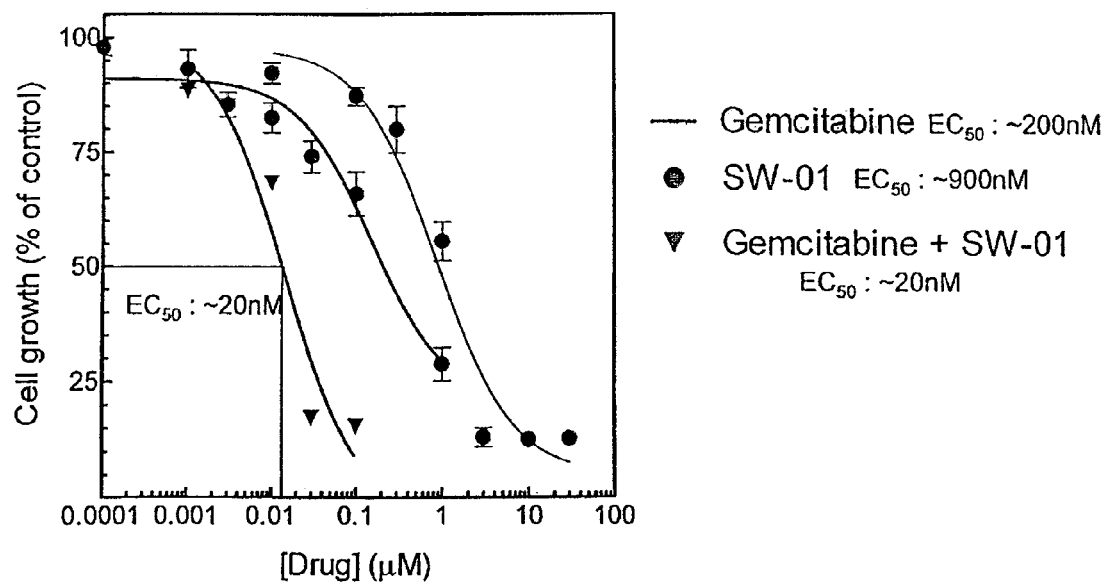

FIG. 5C is a line graph of percentage cell growth relative to control detected by MTT cell proliferation assay versus increasing concentration of SW-01, gemcitabine, or both in combination, in a pancreatic cancer cell line (MiaPaca-2).

Figure 5D:
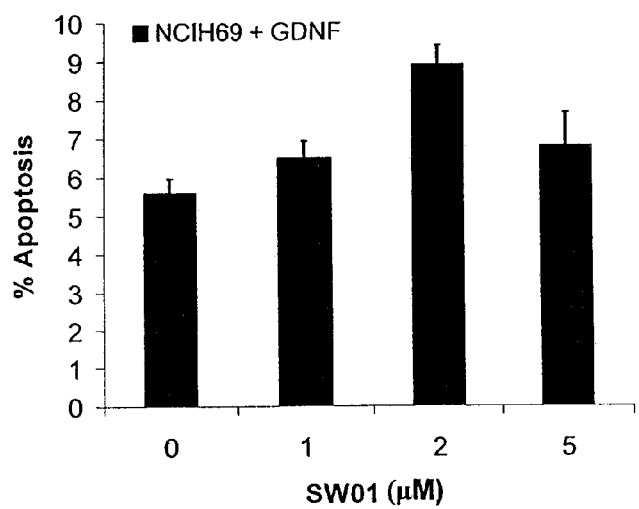

FIG. 5D is a bar graph of percentage apoptosis detected by flow cytometry versus increasing concentration of SW-01 in a small cell lung cancer cell line (NCIH69) in the presence of GDNF.

Figure 5E:
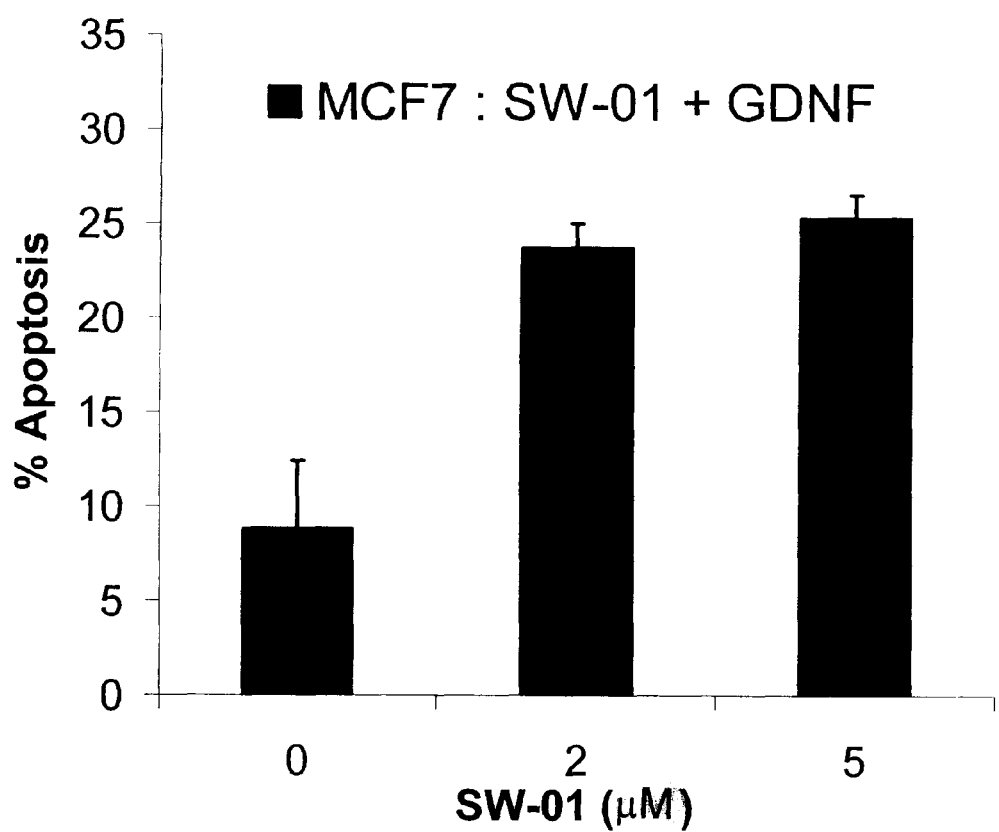

FIG. 5E is a bar graph of percentage apoptosis detected by flow cytometry versus increasing concentration of SW-01 in a breast cancer cell line (MCF7) in the presence of GDNF.

Figure 6:
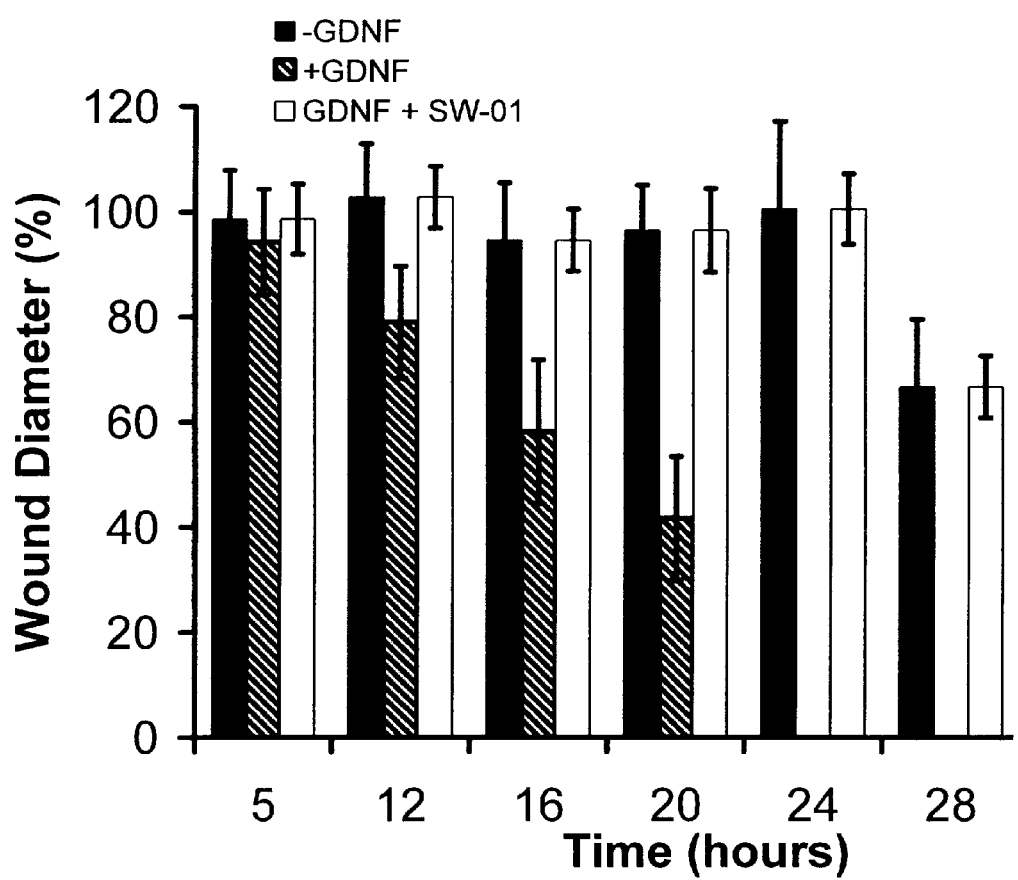

FIG. 6 is a bar graph showing closure of a wound or gap by migration of cells expressing active RET. Bars indicate the remaining percentage of wound area unfilled versus time for RET-containing MiaPaca-2 cells in the presence ("+GDNF") or absence ("−GDNF") of GDNF and in the presence of GDNF and SW-01 (5 μM) ("GDNF+SW-01").

Figure 7:
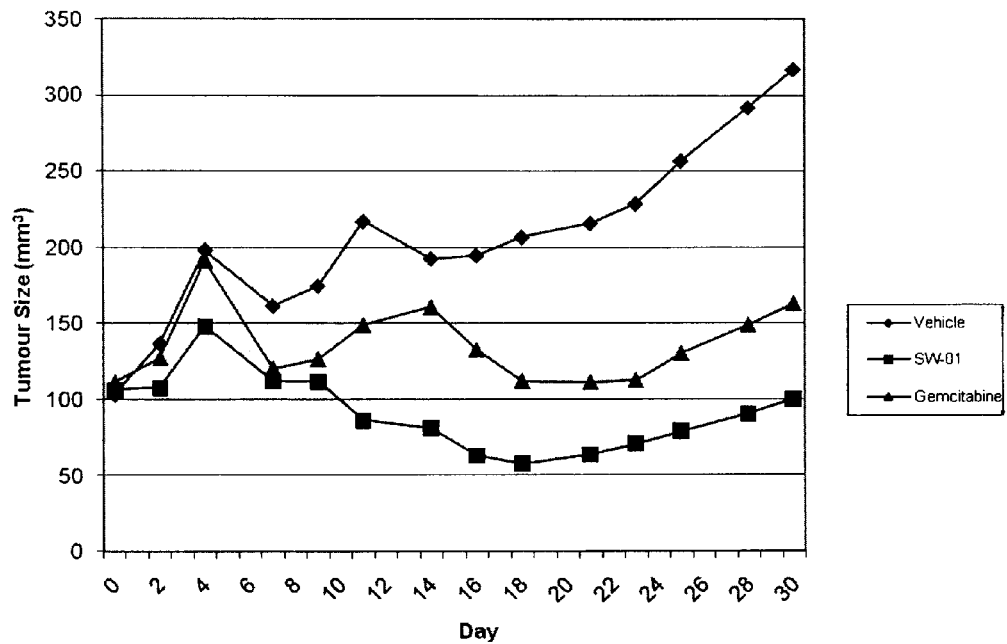

FIG. 7 is a point graph showing a plot of time versus the growth of subcutaneous tumours derived from human pancreatic cell line MiaPaca-2 in nude mice treated with vehicle, SW-01 only, or Gemcitabine only.

Figure 8:
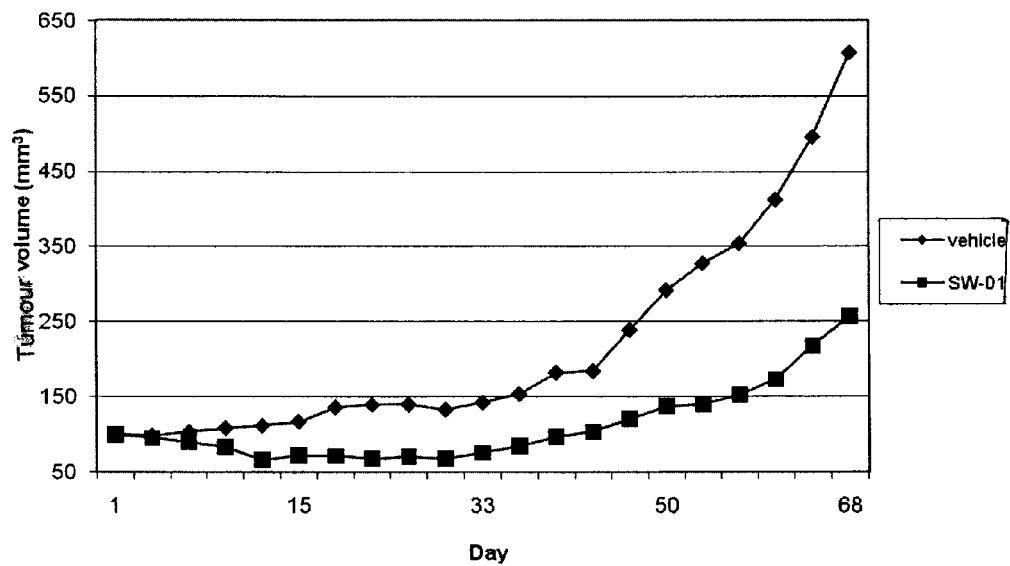

FIG. 8 is a point graph showing a plot of time versus the growth of subcutaneous tumours derived from human pancreatic cell line BxPc3 in nude mice treated with vehicle, or SW-01 only.

Figure 9A:
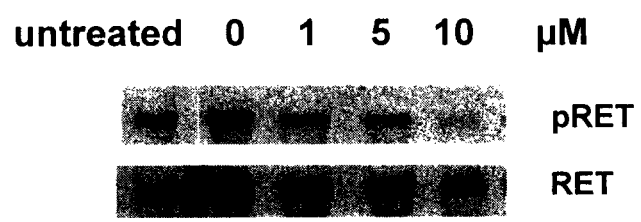

FIG. 9A is an image of western blot assays which demonstrate that norcyclobenzaprine (NCBA) blocked RET activation by GDNF in a concentration dependent fashion.

Figure 9B:
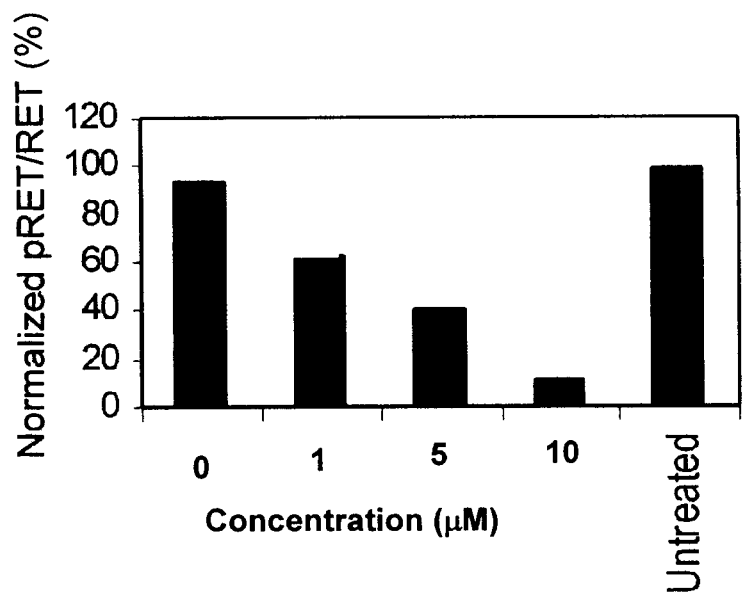

FIG. 9B is a bar graph showing normalized pRET/RET versus concentration of NCBA, demonstrating reduction in RET phosphorylation with increasing concentrations of NCBA.

Figure 10A:
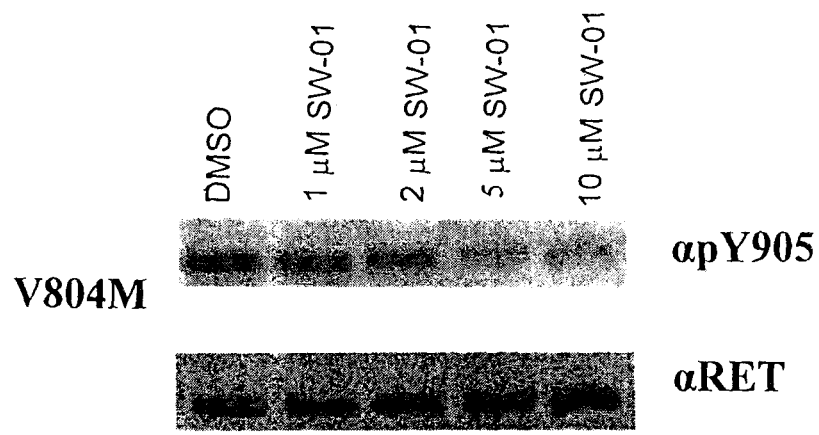

FIG. 10A is an image of western blot assays showing that a cancer causing mutant form of RET (V804M) was inhibited by SW-01 in a concentration dependent fashion.

Figure 10B:
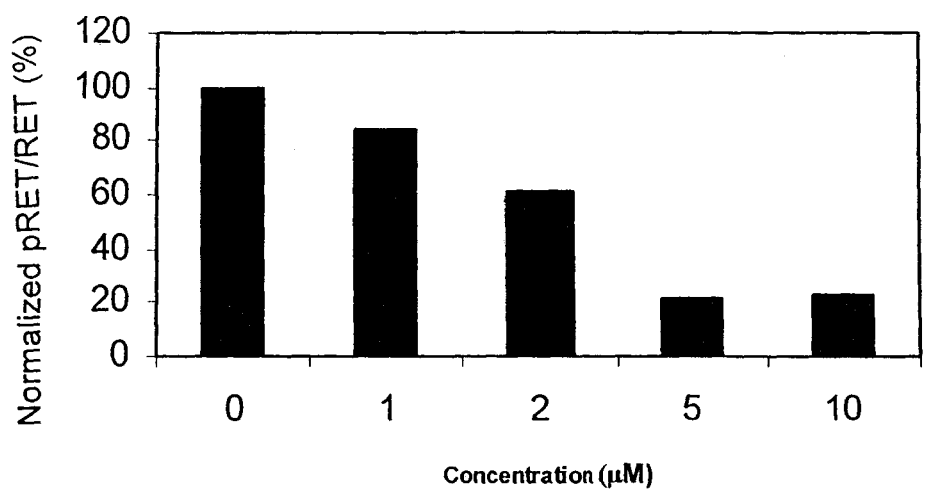

FIG. 10B is a bar graph showing normalized pRET/RET versus concentration of SW-01, demonstrating that there was a decrease in inhibition of the V804M mutant form of RET with increasing concentration of SW-01.

Figure 11A:
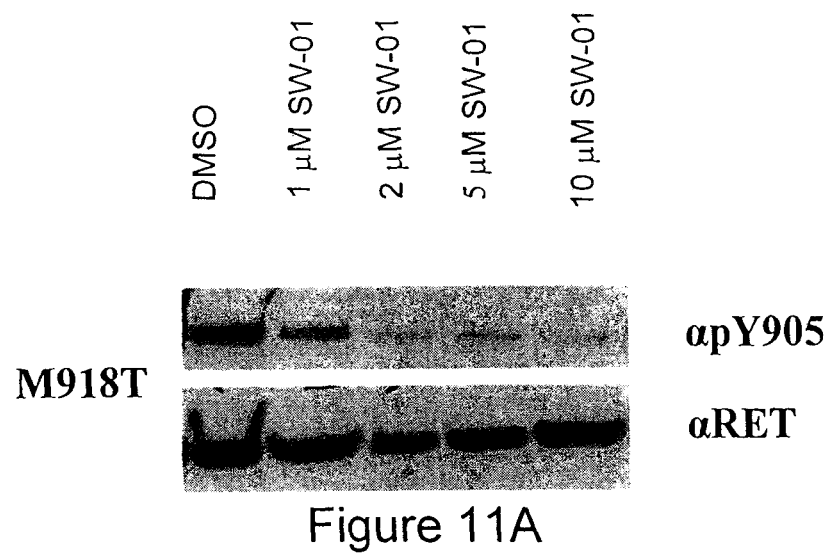

FIG. 11A is an image of western blot assays showing that a cancer causing mutant forms of RET (M918T) was inhibited by SW-01 in a concentration dependent fashion.

Figure 11B:
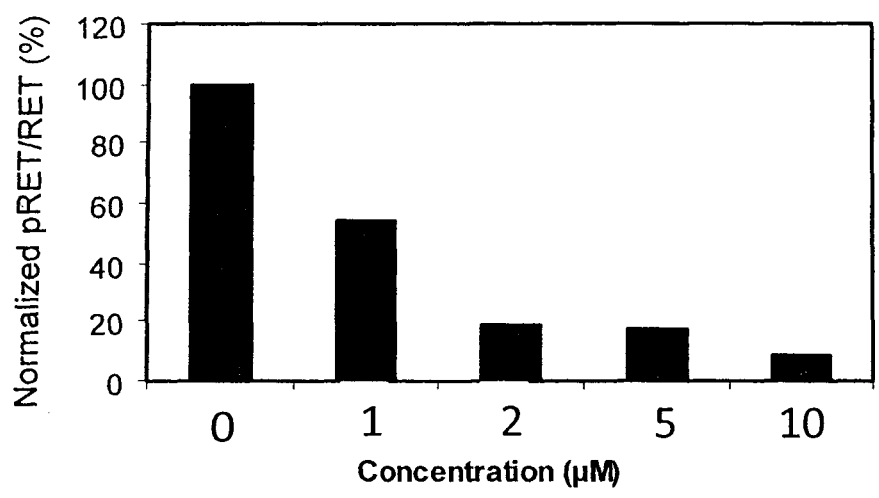

FIG. 11B is a bar graph showing normalized pRET/RET versus concentration of SW-01, demonstrating that there was a decrease in inhibition of the M918T mutant form of RET with increasing concentration of SW-01.

Table 1. Effect of SW-01 on inhibition of various receptor and non receptor tyrosine and serine/threonine kinases.

Table 2. Relative expression of RET in small cell and non small cell lung carcinoma cell lines.

Table 3. Name, structure, median inhibitory concentration ($IC_{50}$) in purified protein assays and median effective concentration ($EC_{50}$) in cell based assays of test compounds.

DETAILED DESCRIPTION OF THE INVENTION

Abbreviations and Definitions

"RET" means the protein encoded by REarranged during Transfection protooncogene which is a receptor tyrosine kinase (RTK) with important roles in cell growth. "Phospho-RET" and "pRET" mean phosphorylated RET, and are used interchangeably. A "pan RET" antibody means an antibody that recognizes both phosphorylated and unphosphorylated RET, i.e., all RET.

"icRET" means a chimeric fusion protein including the intracellular portion (amino acid 658 to the COOH terminus) of RET and a dimerization domain created with the ARGENT™ regulated homodimerization kit available from ARIAD, Cambridge, Mass., USA. The icRET expression construct is described in Richardson, D. S. et al., Oncogene (2006) 25: 3206-3211 and Hickey, J. G. et al., Genes Chrom Canc (2009) 48:429-440. This construct when expressed provides a RET kinase lacking the extracellular ligand-binding domain that can be activated by using an artificial dimerizing agent known as AP20187. Dimerization is typically induced 30 minutes prior to harvesting using 1 mM AP20187 dimerizer.

"RET-associated cancer" as used herein means a malignant growth or tumor that derives directly or indirectly from expression of RET, mutation of the RET gene, or post-translational modification of RET that results in altered function. In the case of expression, aberrant expression is also included, e.g., altered level of expression (such as, e.g., constitutive expression, upregulation, and constitutive overexpression), as well as location of RET expression (cellular or tissue). In the case of mutation, there is included, without restriction, point mutation, and addition or deletion of RET residue(s), as well as chimeric RET proteins (i.e., derived from chromosomal translocation or rearrangement, e.g., RET or RET domain(s) fused to oncogene or oncogene domain(s)). Such mutation also includes RET gain-of-function mutation, and RET activation mutation. Such mutation of the RET gene also includes mutation in a regulatory region or element (e.g., enhancer, promoter) and may for example result in constitutive expression or upregulation of RET. Such mutation of the RET gene also includes "resistance mutations", i.e., mutant forms of the RET protein that do not efficiently bind and thus are not efficiently inhibited by certain inhibitors. Also included are mutations that regulate binding to RET of molecules other than inhibitors, for example ATP to the ATP binding site.

"ERK" means extracellular-signal-regulated kinase, an important signaling molecule. "pERK" means phosphorylated ERK. "MTC" means medullary thyroid carcinoma, a type of thyroid cancer that arises from C-cells. "SKNBE(2)" is a human neuroblastoma cell line. "TT" and "TPC-1" are thyroid cancer cell lines. "HEK293" is an embryonic kidney cell line. "MTT" means 3-(4,5-dimethylthiazol-2-yl)-2,5-diphenyltetrazolium bromide. "FACS" means fluorescence-activated cell sorting. "MEN 2" means multiple endocrine neoplasia type 2, a severe form of familial endocrine cancer that is characterized by early onset of endocrine tumours and a broad range of developmental abnormalities. "FLT-3" means FMS-like tyrosine kinase 3. "PDAC" means pancreatic ductal adenocarcinoma. "BRAE" means v-raf murine sarcoma viral oncogene homolog β1, a protein involved in cell signaling and in cell growth.

As used herein, the term "amount" is intended to refer to the quantity of RET inhibitor administered to a subject. The term "amount" encompasses the term "dose" or "dosage", which is intended to refer to the quantity of RET inhibitor administered to a subject at one time or in a physically discrete unit, such as, for example, in a pill, injection, or patch (e.g., transdermal patch). The term "amount" also encompasses the quantity of RET inhibitor administered to a subject, expressed as the number of molecules, moles, grams, or volume per unit body mass of the subject, such as, for example, mol/kg, mg/kg, ng/kg, ml/kg, or the like, sometimes referred to as concentration administered.

The term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

RET and Cancer

RET (REarranged during Transfection) proto-oncogene encodes a receptor tyrosine kinase which plays an important role in cell growth, differentiation and survival (see Attie-Bitach, T. et al., *Am. J. Med. Genet.,* 80: 481-486 (1998); Avantaggiato, V. et al., *Cell Growth and Differentiation,* 5: 305-311 (1994); Pachnis, V. et al., *Development,* 119: 1005-1017 (1993); Schuchardt, A. et al., *Nature,* 367:380-383 (1994); and Takahashi, M. et al., *Oncogene,* 3:571-578 (1988)). RET is composed of an extracellular region which binds its ligands, a transmembrane region and an intracellular (cytoplasmic) kinase domain that is responsible for autophosphorylating intracellular tyrosine residues that interact with proteins involved in downstream cell signaling. Autophosphorylation occurs at multiple tyrosine residues in the C-terminal domain such as, e.g., 1062. RET's downstream targets include the Ras/Erk kinase, PI3 kinase/Akt, p38MAP kinase, PLC-γ, JNK, STAT, Erk5 and Src signaling pathways (see Santoro et al., *Endocrinol.* (2004) 145: 5448-5454; Arighi et al., *Cytokine Growth Factor Rev.* (2005) 16: 441-467; and Kodama et al. *Cancer Sci.,* (2005) 96: 143-148).

RET has been implicated in a variety of cancers, indicating that it may be an important prognostic marker for cancer and a potential target for anti-invasion therapy. For example, RET signaling is known to promote proliferation, survival and cell scattering of breast cancer cells (Meric, F. et al., *Clin. Cancer Res.* (2002) 8: 361-367, and Esseghir, S. et al., *Cancer Res.* (2007) 67: 11732-11741). Constitutively activating mutations of RET cause multiple endocrine neoplasia 2 (MEN 2), an inherited cancer syndrome characterized by medullary thyroid carcinoma (MTC) (Mulligan, L. M. et al., *Nature* (1993) 363: 458-460). RET is also mutated in 50-70% of sporadic MTC and 30-70% of sporadic papillary thyroid carcinoma. In each case, these mutations result in inappropriate activation of RET and a constitutive stimulation of RET signaling (reviewed Lai et al. *Endocr. Pathol.* (2007) 18:57-67). The upregulation of wildtype RET signals has also been linked to increased invasiveness in pancreatic carcinoma (Funahashi et al. *J. Surg. Oncol.* (2005) 91: 77-83) and recently we have recognized an increase in wildtype RET signaling as a major contributor to development of pheochromocytoma (Lai et al., *Endocr. Pathol.* (2007) 18:57-67). Further activation of RET by radiation induced mutations leading to thyroid cancer has been a major clinical outcome of the Chernobyl incident (Nakashima (2007) *Hum. Pathol.* 38: 621-628).

Constitutive activation as well as aberrant upregulation of RET have been associated with tumour progression and/or invasion in multiple tumour models. Activated RET has been shown to transform cells and generate tumours in nude mice. Additional examples of the connection between RET and cancer include the following:

(a) in over 50% of people with medullary thyroid carcinoma and 90% of people with MEN 2, gain-of-function mutations in RET proto-oncogene have been implicated (see Mulligan, L. M. et al., *J. Clin. Endo. Metab.* (1995) 80: 1989-1995).

(b) in 57% of SCLC and in a subset of NSCLC, RET and its co-receptors are expressed (Mulligan, L. M. et al., *Genes Chrom Canc* (1998) 21: 326-332); in lung cancer, activating mutations in RET have been identified and may promote tumour progression (Thomas, R. K. et al., *Nature Genet.* (2007) 39: 347-351);

(c) in pancreatic cell lines, GDNF family ligand (GFL) activation of RET has been implicated in an increase in cell proliferation and/or cell invasiveness (Okada, Y. et al., *Int. J. Cancer,* (1999) 81: 67-73; Ceyhan, G. O. et al., *Ann. Surg.,* (2006) 244: 274-281; Ito, Y. et al., *Surgery,* (2005) 138: 788-794);

(d) in studies of patients with pancreatic ductal adenocarcinoma, strong GDNF and RET expression was correlated to invasion and reduced patient survival after surgical resection (Sawai, H. et al., *Cancer Res.* (2005) 65: 11536-11544);

(e) by screening a tissue microarray of invasive breast tumors, it was shown that RET and GFRalpha 1 were overexpressed in a subset of estrogen receptor-positive tumours (see Meric, F. et al., *Clin. Cancer Res.* (2002) 8: 361-367; and Esseghir, S. et al., *Cancer Res.* (2007) 67: 11732-11741);

(f) RET mutations are also found in a significant proportion of adrenal tumours, primarily pheochromocytoma (PC) (Neumann H. P. et al., *N Engl J Med* (2002) 346: 1459-1466);

(g) increased expression of RET has also been noted in neuroblastomas, lung tumours, seminomas; and (h) one of the more aggressive and lethal pancreatic cancers is RET-associated pancreatic ductal adenocarcinoma (see Bardeesy, N. et al., *Nat. Rev. Cancer* (2002) 2: 897-909).

Activation of RET is a multistep process, involving interaction with a soluble ligand and a non-signaling cell surface-bound molecule. RET-activating ligands have been shown to induce pancreatic cell invasiveness in cell line studies. Known RET-activating soluble ligands belong to the glial cell line-derived neurotrophic factor (GDNF) family of ligands (GFL) and include GDNF, neurturin, persefin and artemin (see Airaksinen, M. S. et al., *Mol. Cell. Neurosci.* (1999) 13: 313-325). The cell surface-bound molecules belong to the GDNF family receptor alpha (GFRalpha) proteins and are attached to the cell membrane by a glycosyl-phosphatidylinositol linkage (see Takahashi, M., *Cytokine Growth Factor Rev.* (2001) 12: 361-373). GFL and GFRalpha family members form complexes which, in turn, bind to RET and trigger its activation by causing it to dimerize (Takahashi, 2001). Dimerization facilitates trans-autophosphorylation of specific tyrosine residues in the RET intracellular domain. Activation of RET, in turn, stimulates a cascade of intracellular protein interactions.

RET has been shown to interact with, and activate, β-catenin. As described in Gujral et al. (*Cancer Res.* (2008) 68: 1338-1346), RET binds to and phosphorylates β-catenin. The interaction between RET and β-catenin can be direct and independent of cytoplasmic kinases, such as SRC. As a result of RET-mediated tyrosine phosphorylation, β-catenin escapes cytostolic downregulation by APC/Axin/GSK3 complex and accumulates in the nucleus, where it can stimulate β-catenin-specific transcriptional programs in a RET-dependent fashion. Downregulation of β-catenin activity decreases RET-mediated cell proliferation and colony formation. Also described in Gujral et al., (2008), a transplantation mouse model is used to show that RET and β-catenin coexpression drives tumour formation and increases invasiveness.

A RET-β-catenin signaling pathway plays a role in RET-mediated cell proliferation, as well as in tumour formation, invasion and metastasis. This pathway may provide a new, specific therapeutic target for RET-associated cancers.

RET Inhibitors

A number of tyrosine kinase inhibitors have been demonstrated to inhibit RET activity. Some of these small molecule antagonists block access to the adenosine tri-phosphate (ATP) binding site, a highly conserved region. These inhibitors have been shown to inhibit a broad spectrum of kinases, including RET. In addition, some constitutively active mutants of RET are resistant to these inhibitors. Without wishing to be bound by theory, the inventors suggest that this resistance may be because of activating mutations of RET within regions that are critical for inhibitor binding.

Some small molecules are currently in clinical trials for thyroid cancer. ZD6474 ("vandetanib" or 4-anilinoquinazoline) is a VEGFR inhibitor, which also has activity against RET. Pyrazolopyrimidines PP1 and PP2 have also been reported to inhibit wild type RET (Carlomagno, F. et al. *Oncogene* (2000) 6056-6063). 17-AAG is an HSP90 inhibitor that acts indirectly by blocking a key chaperone responsible for RET maturation. SU11248 ("sunitinib") is an oral small molecule tyrosine kinase inhibitor of VEGFR, PDGFR, KIT and FLT-3, and also is a highly active inhibitor of RET ($IC_{50}$ 224 nm) (see Chow, L. Q. et al., *J. Clin. Oncol.*, (2007) 25: 884-896; Kim, D. W. et al., *J. Clin. Endocrinol. Metab.*, (2006) 91: 4070-4076; and Polyzos, A. *J. Steroid Biochem. Mol. Biol.*, (2008) 108: 261-266). In addition, BAY 43-9006 ("sorafenib") is an oral multikinase inhibitor initially developed as a specific inhibitor of BRAF (which is a protein involved in cell growth) (see Wilhelm, S. et al., *Nat. Rev. Drug Discov.*, (2006) 5: 835-844; and Lyons, J. F. et al., *Endocr. Relat. Cancer*, (2001) 8: 219-225). It also inhibits other kinases including VEGFR-2, VEGFR-3, PDGFR, c-kit, and FMS-like tyrosine kinase 3 (see Adnane, L. et al., *Methods Enzymol.*, (2006) 407: 597-612; Zhang, W. et al., *J. Natl. Cancer Inst.*, (2008) 100: 184-198) and RET (see Carlomagno, F. et al., *J. Natl. Cancer Inst.*, (2006) 98: 326-334).

However, until now, a small molecule RET inhibitor with high specificity for RET, and with efficacy for common RET activating mutants, has not been identified. An aspect of the invention is a family of RET-inhibiting small molecules that are highly specific for RET, and that have efficacy for common mutants in which RET is activated. Of particular note, one of these compounds, SW-01, was shown to be RET-specific with an $IC_{50}$ of 300 nM. Embodiments of the invention provide methods and pharmaceutical compositions comprising compounds of Formula (1A), (1B) and (1C) for the treatment and/or mitigation of cancer.

A compound of Formula (1A) for the treatment and/or mitigation of cancer is depicted as follows:

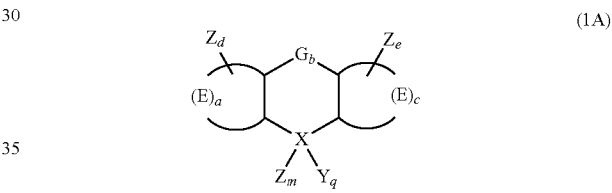

(1A)

where G is S, O, NH, CH$_2$, CR$^1$R$^2$—CR$^1$R$^2$, CH═CH, CR$^1$═CR$^2$, N═CH, N═N, O—CH$_2$, CH$_2$—CH$_2$, O—O, S—CH$_2$, S—S, or

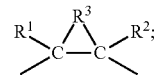

R$^1$ and R$^2$ are independently H, alkyl, and halo;
R$^3$ is CH$_2$, CR$^1$R$^2$, S, or NR$^4$;
X is sp$^2$ hybridized carbon, sp$^3$ hybridized carbon, or sp$^3$ hybridized nitrogen;
Y is sp$^2$ hybridized nitrogen, sp$^3$ hybridized nitrogen, sp hybridized carbon, sp$^2$ hybridized carbon, sp$^3$ hybridized carbon, amino, NR$^4$R$^5$, O, S, P, ester, amide, keto, hydroxyl, N$^+$R$^6$R$^7$O$^-$, substituted or unsubstituted aryl, halo, nitro, carboxyl, substituted alkyl (such as, for example, aminoalkyl, halogenated alkyl), unsubstituted alkyl, or a combination thereof;
R$^4$ and R$^5$ are independently H or alkyl;
R$^6$ and R$^7$ are independently alkyl;
E is independently sp$^2$ hybridized carbon, sp$^2$ hybridized nitrogen, sp$^3$ hybridized carbon, or sp$^3$ hybridized nitrogen, and forms a saturated or unsaturated ring system optionally with a heteroatom as a ring atom;
Z is independently H, aryl, halo, nitro, hydroxyl, amino, thiol, alkoxyl, amido, amide, carboxyl, alkenyl, allyl, cyano, substituted alkyl (such as, for example, alkylamino, halogenated alkyl), or unsubstituted alkyl;

a is 0-5;
b is 0-1;
c is 0-5;
d is 0-7;
e is 0-7;
m is 0-1; and
q is 1-2.

Another embodiment of the invention provides compounds of the following Formula (1B) for the treatment and/or mitigation of cancer:

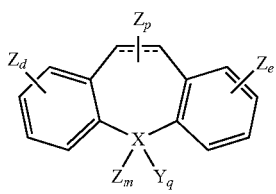

(1B)

where X, Z, Y, m, d, e, and q are as defined previously; p is 0-2, and the dotted line indicates that the compounds may be saturated or unsaturated at this location.

Another embodiment of the invention provides compounds of the following Formula (1C) for the treatment and/or mitigation of cancer:

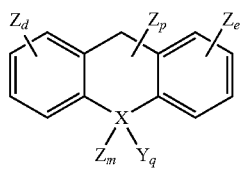

(1C)

where X, Z, Y, m, d, e, p and q are as defined previously.

Previously, a three-dimensional model of a RET kinase domain was developed in silico (see Gujral, T. S. et al., *Cancer Res.* (2006) 66: 10741-10749). Parameters obtained from this model agreed with predictions based from X-ray crystal structure data of RET and related kinases (Knowles, P. P. et al., *J. Biol. Chem.*, (2006) 281: 33577-33587). The model's parameters were used to predict functional effects of certain activating RET mutations.

This validated model was used to screen (virtually) for small molecules that could bind to active sites of RET. Such screening was performed using a structure-guided docking strategy obtained from a software program module called FlexX of a computer program called SYBYL® (available from Tripos Inc., St. Louis, Mo., USA). A diverse library of small molecules were screened (virtually) by attempting to dock them to RET's active sites using this software. Structural information for these small molecules was obtained from the Developmental Therapeutics Program at National Cancer Institute/National Institutes of Health (NCI/NIH) of the United States of America (see the world wide web website at "http://dtp.nci.nih.gov/" for more information). This library of 1900 structurally diverse small molecules has pharmacophores in it which are described by NCI/NIH as representative of their repository of more than 140,000 non-discrete synthetic and natural products.

Using the structure-guided docking strategy, 238 small molecules that docked to RET at various sites were identified. Following knowledge-based filtering, three of the 238 compounds were predicted to bind to RET at its activation loop region. These three compounds were known in the NCI/NIH database as NSC 10777, NSC 78206 (also known as cyclobenzaprine, Flexeril™, and known herein as "SW-01"), and NSC 27476.

A first problem with certain known inhibitors of RET kinase is that they generally inhibit a number of related kinases, often more strongly than they inhibit RET (de Groot, J. W. et al., *Endocr. Rev.* (2006) 27: 535-560). Broad spectrum kinase inhibitors have demonstrated cardiotoxicity and hypertension. Clinically, a narrower spectrum of inhibited kinases is expected to mean a reduced number of unwanted side effects. A second problem with certain known inhibitors is resistance. Common mutations within the ATP-binding site of RET kinase (e.g. V804M, V804L), where the inhibitors would normally bind, alter the ATP-binding domain structure and prevent the inhibitors from binding. Since the three compounds NSC 10777, NSC 78206 (known herein as SW-01), and NSC 27476 were predicted to bind to residues within the RET activation loop, they were predicted to be highly selective for RET kinase. The residues of the RET activation loop do not include, or directly interact with, any residues known to be mutated in activated RET. Thus, no known RET mutants are predicted to have a priori resistance to such inhibitors.

Figure 1:
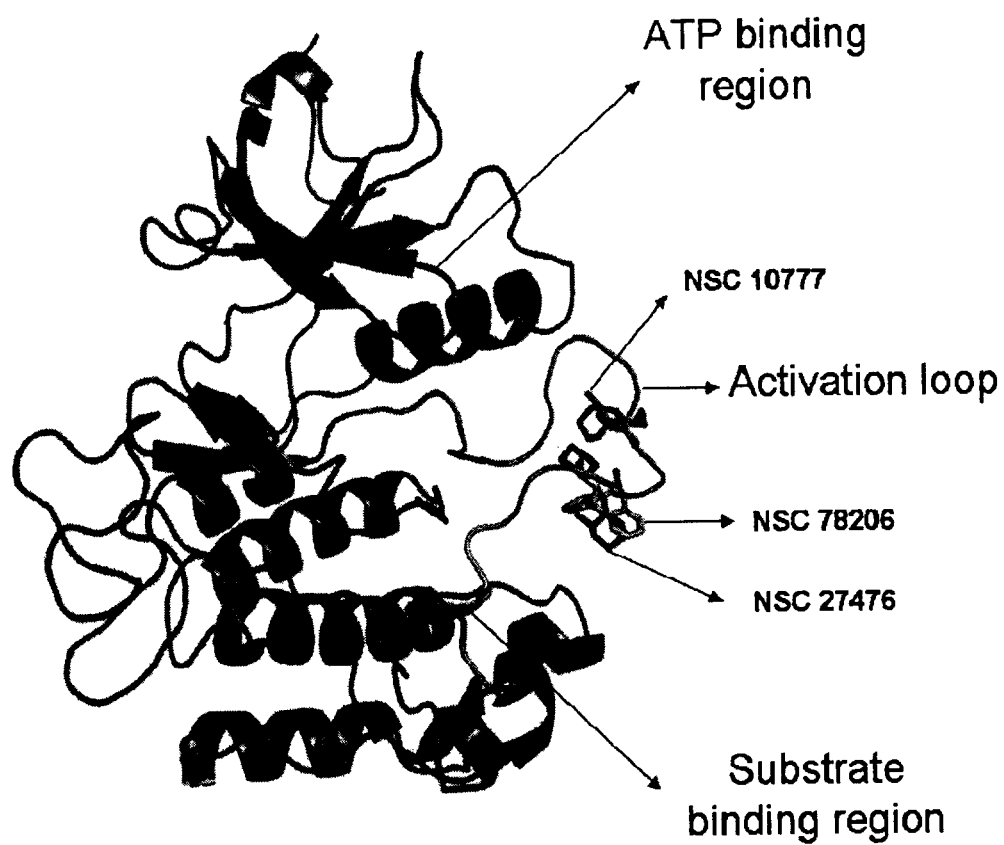

Referring now to FIG. 1, this figure shows a ribbon diagram of the intracellular domain of wildtype RET (residues 709-988) in its active conformation, as well as interaction of the active conformation's activation loop region of RET with compounds NSC 10777, NSC 78206, and NSC 27476. The activation loop region has low homology to other kinases, but is considered critical to RET activation (Knowles, P. P. et al., *J. Biol. Chem.* (2006) 281: 33577-33587; and Tuccinardi, T. et al., *J. Chem. Inf. Model* (2007) 47: 644-655). See Gujral et al., *Cancer Res.* (2006) 66: 10741-9 for more information on this three-dimensional model of RET.

Figure 2A:
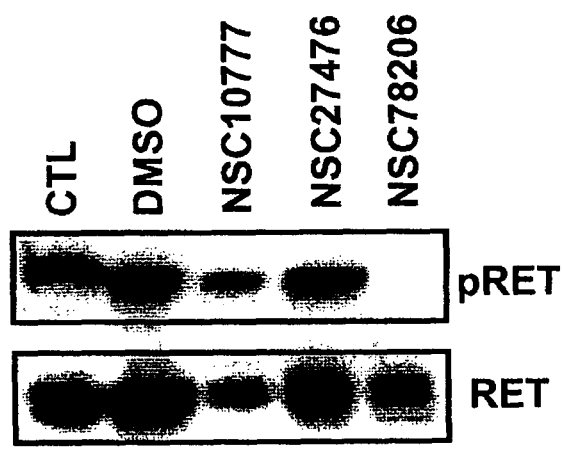

Since the three compounds, NSC 10777, NSC 78206 (known herein as "SW-01"), and NSC 27476 were predicted to bind to the activation loop region of RET, they were chosen as candidate compounds for laboratory testing to determine if they could provide both effective and specific RET inhibition. Descriptions of the laboratory tests that were conducted are described in the Working Examples and their results are presented in the figures and tables. As seen in FIG. 2A, the presence of NSC78206 caused significant RET inhibition in HEK293 cells expressing RET. Further studies were conducted to study the inhibition and selectivity of SW-01 for RET. Also, several compounds of Formula (1A) were tested to quantify their ability to provide RET inhibition. The structures of these compounds, known herein as SW-01 to SW-09 and SW-11 to SW-13, are presented in Table 3 together with their chemical names, Chemical Abstracts Service numbers, $IC_{50}$ (concentration of inhibitor at half maximal activity in purified protein assay) and $EC_{50}$ (concentration of inhibitor at half maximal activity in cell based system) values.

SW-01

A RET kinase inhibitor, SW-01, that is specific to the product of the RET proto-oncogene with an $IC_{50}$ of 300 nM has been identified. This small molecule inhibits RET autophosphorylation and blocks the neoplastic growth and proliferation of thyroid cancer cell lines. Therefore, it is expected to be useful for inhibiting survival and proliferation of tumour cells. It has been further tested in pancreatic cancer and SCLC cell lines. This compound blocks RET autokinase activity in recombinant protein tests and in cell based assays. Structurally similar compounds are described, with $IC_{50}$ and $EC_{50}$ values. Pharmaceutical compositions comprising an effective amount of SW-01 for treating cancer and for inhibiting tumour growth are described, as well as methods for treating cancer and for inhibiting tumour growth employing same. The inventors also reasonably expect that pharmaceutical compositions and methods employing an effective amount of SW-01 could show utility for preventing cancer and for preventing tumour growth.

A synthetic route to SW-01 is described in Villani, F. J. et al., *J. Med. Pharm. Chem.* (1962) 5: 373-383. Cyclobenzaprine was approved by the U.S. Food and Drug Administration in 1977 for treatment of acute muscle spasms of local origin. Cyclobenzaprine hydrochloride is sold for use as a skeletal muscle relaxant. Its pharmacokinetics are discussed in Katz, W. et al., *Clin. Thera.* (1988) 10: 216-228.

At least one aspect of the invention relates to the RET kinase inhibitor cyclobenzaprine, whose chemical name is 3-(5H-dibenzo[a,d]cyclohepten-5-ylidene)-N,N-dimethyl-1-propanamine and which is known herein as "SW-01". SW-01 provided significant RET inhibition in kinase assays (307 nM) using purified recombinant RET proteins. Although not wishing to be bound by theory, the inventors suggest that the effectiveness of compounds of Formula (1A) to inhibit RET autophosphorylation is due to their ability to interfere with the RET activation loop's mobility, which is considered critical for activation. Specifically, based on computer modelling of a complex of SW-01 and RET, it is believed that SW-01 binds non-covalently to two tyrosine residues in the RET activation loop, specifically, residues Y900 and Y905.

As shown in the figures and discussed below, RET phosphorylation is blocked or dramatically reduced in the presence of SW-01 in cell based assays using cells overexpressing RET, and in a human medullary thyroid carcinoma cell line. This human medullary thyroid carcinoma cell line, known herein as "TT", expresses an endogenously activated RET mutant. In the presence of SW-01, significant decreases in cell proliferation and colony formation were observed in RET-expressing HEK293cells. Accordingly, SW-01 is a RET kinase inhibitor with promising clinical utility.

Referring to FIG. 2A, compounds NSC 10777, NSC 78206 (also known herein as "SW-01"), and NSC 27476 were tested to study their ability to interfere with the activation of RET protein. Details of the study are described in Example 2A. Briefly, HEK293 cells expressing RET were treated with GDNF and the indicated test compounds and proteins harvested to study the effect of NSC 10777, NSC 78206, and NSC 27476 on RET autophosphorylation. Autokinase activity of RET was measured using an anti-phosphoRET antibody, pY905, which recognizes phosphorylation of RET at residue Y905. Residue Y905 is a primary phosphotyrosine which lies in the activation loop of the kinase and is involved in RET autophosphorylation and subsequent activation. Levels of total RET were detected using a pan-RET antibody. In summary, this study demonstrated that NSC 78206 (SW-01) did not affect the expression levels of RET but significantly reduced its autophosphorylation (also known as autokinase) activity.

Figure 2B:
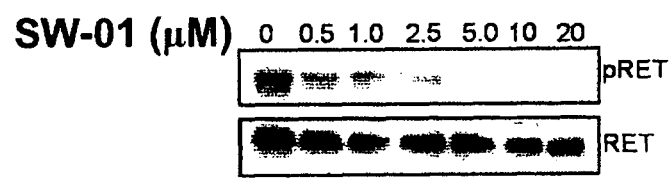

Referring to FIG. 2B, SW-01 was tested for its ability to interfere with the activation of recombinant RET protein in in vitro kinase assays using purified recombinant RET proteins that were functionally validated previously (see Gujral, T. S., *Cancer Res.*, (2006) 66: 10741-10749), As above, autokinase activity of RET was measured using anti-phosphoRET antibody pY905 and total RET was assessed using a pan-RET antibody. Details of this study are provided in Example 2B. This study demonstrated that SW-01 significantly reduced RET autophosphorylation.

Figure 2C:
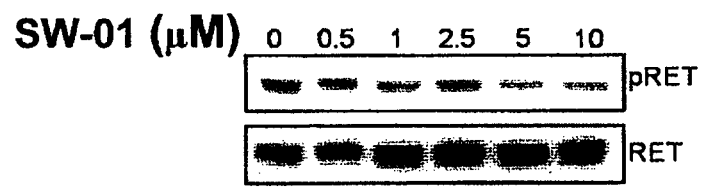

Referring to FIG. 2C, a cell based assay was used to study the effect of SW-01 on RET autophosphorylation. Details are provided in Example 2C. In brief, RET phosphorylation was blocked or dramatically reduced upon SW-01 treatment in a concentration-dependent manner. This cell based study demonstrated that SW-01 is a RET inhibitor that blocks autokinase activity but that does not affect expression levels of RET.

Figure 2D:
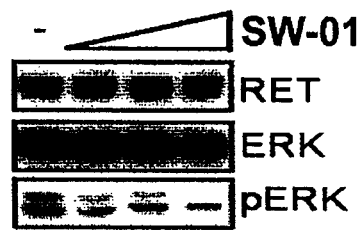

Referring to FIG. 2D, effects of SW-01 on downstream signaling pathways were investigated. Upon activation, (uninhibited) RET transduces downstream signals through phosphorylation of multiple intracellular tyrosines, and has been shown to activate RAS-ERK, JNK, PI3K, p38MAPK, SRC and ERK5 signaling pathways (see Arighi, E. et al., *Cytokine Growth Factor Rev.* (2005) 16: 441-467. These signaling pathways result in cell proliferation, cell differentiation, or transformation (see Arighi, E. et al., *Mol. Endocrinol.* (2004) 18:1004-1017; and Tang, M. J. et al., *J. Cell Biol.* (1998) 142:1337-1345). Of these downstream pathways, RAS-ERK was selected for study. Details of the study are provided in Example 2D. In summary, it was shown that SW-01 blocks RET-mediated activation of ERK without affecting its expression levels (see FIG. 2D).

In other studies in parental HEK 293 cells that do not express RET, treatment with increasing concentration of SW-01 did not affect ERK or AKT pathways, indicating that SW-01 is a RET-specific inhibitor.

Figure 3A:
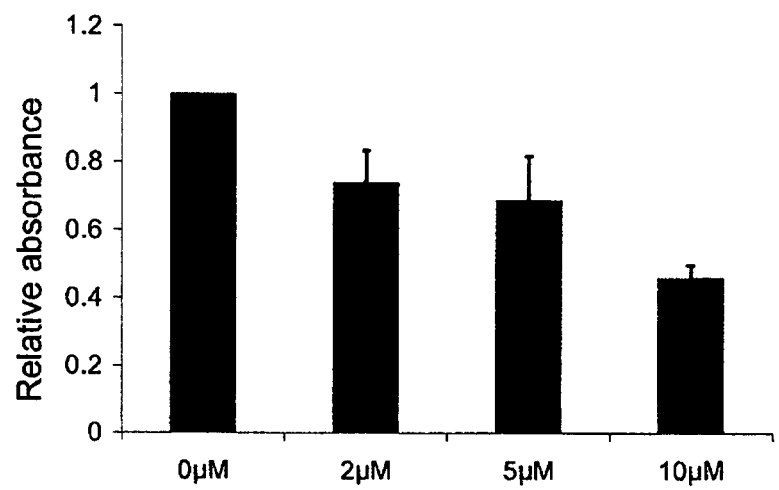
FIG. 3A is a bar graph of relative absorbance versus concentration of SW-01 that shows the effects of SW-01 on cell growth as measured by a 3-(4,5-dimethylthiazol-2-yl)-2,5-diphenyltetrazolium bromide (MTT) cell proliferation assay. Cell growth is measured using MTT dye uptake and colour read-out and is expressed as a ratio of growth in the presence and absence of SW-01.
Figure 3B:
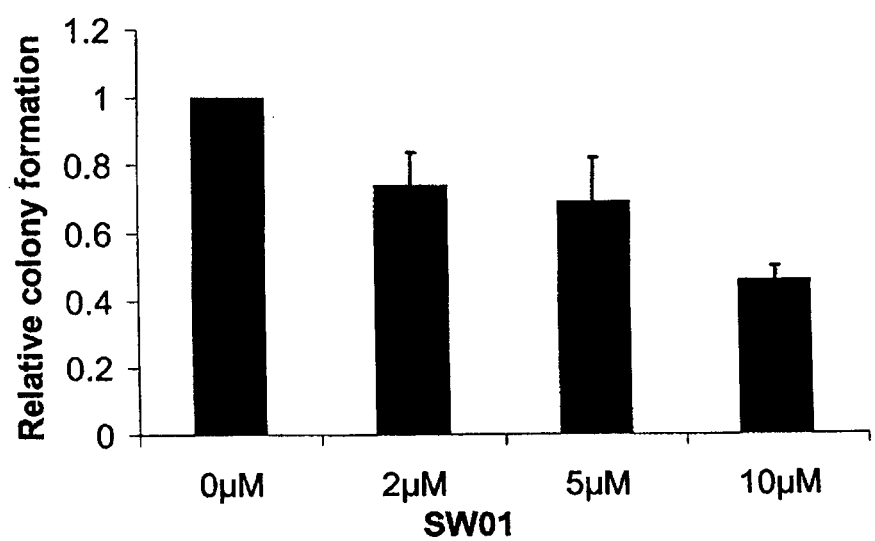
FIG. 3B is a bar graph showing relative colony formation of RET-expressing HEK293 cells in a soft agar assay, versus concentration of SW-01. Colony formation is expressed as relative mean colony number in the presence and absence of SW-01 with standard deviation for a minimum of three replicate experiments.
Figure 3C:
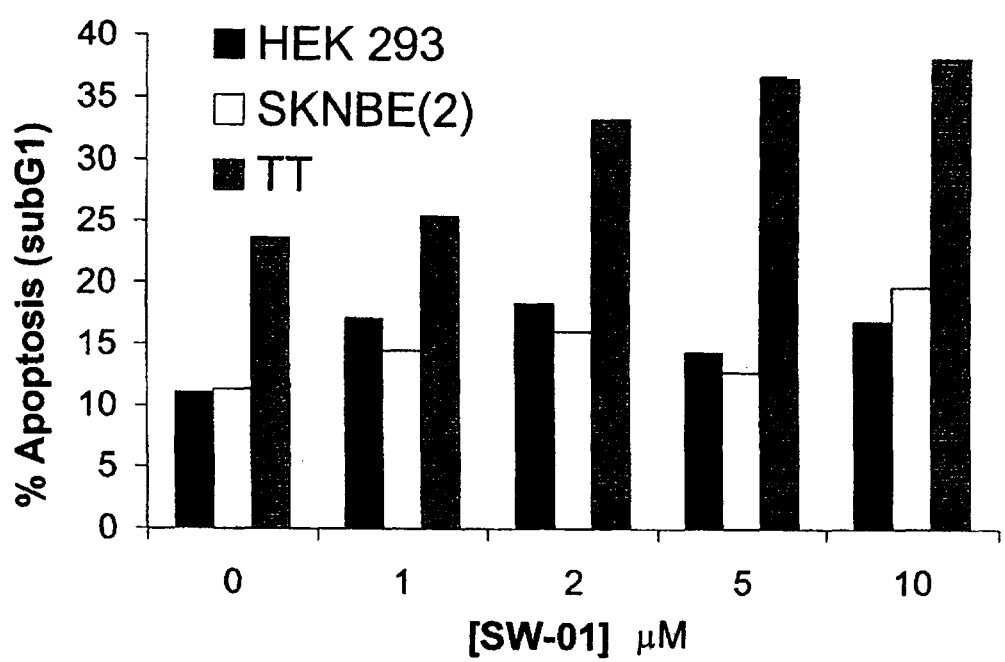
FIG. 3C is a bar graph of percentage apoptosis versus concentration of SW-01 for three cell lines, specifically, HEK293, TT, and SKNBE(2) detected by flow cytometry.

Referring to FIGS. 3A-C, biological effects of SW-01 on RET-mediated oncogenesis were investigated. FIG. 3A shows results of an MTT cell proliferation assay in the absence and presence of varying concentrations of SW-01. FIG. 3B shows results of a colony formation assay in RET-expressing HEK293 cells in soft agar in the absence and presence of varying concentrations of SW-01. FIG. 3C shows dramatic results of an apoptosis assay of a thyroid carcinoma cell line, TT. This line is derived from a thyroid cancer caused by activated mutant RET and shows a large increase in apoptosis, or cell death, in the presence of SW-01.

Referring to FIG. 4, SW-01 and four structurally similar analogs of SW-01 were tested to determine their effect on RET autophosphorylation using HEK293 cells. Two of the test compounds, SW-03 and SW-04, did not affect RET autophosphorylation, while SW-02 and SW-05 inhibited RET activity.

Referring to FIGS. 5A, D and E, graphs are shown indicating percentage cell apoptosis results for several cancer cell lines in the presence of SW-01, including pancreatic cancer cell line (MiaPaca-2, see FIG. 5A), small cell lung cancer cell line (NCIH69, see FIG. 5D), and breast cancer cell line (MCF7, see FIG. 5E).

Referring to FIG. 5B, graphs are shown indicating percentage cell growth detected by MTT cell proliferation assay versus concentration of SW-01 in pancreatic cancer cell lines (MiaPaca-2 and BxPc3). Notably, treatment with SW-01 reduced cell proliferation in both MiaPaca-2 and BxPc3 cell lines.

Referring to FIG. 5C, a graph is shown indicating percentage cell growth detected by MTT cell proliferation assay versus concentration of SW-01, gemcitabine, or both in a pancreatic cancer cell line (MiaPaca-2).

Referring to FIG. 6, a bar graph is shown that plots relative wound diameter versus time. This figure graphically illustrates closure of a wound or gap by migration of cells expressing active RET. Specifically, bars indicate the remaining percentage of wound diameter versus time for RET-containing MiaPaca-2 cells in the presence or absence of GDNF and in the presence of GDNF and SW-01. Failure of wounds to close (i.e., area of wound space remaining after time) indicates that cell migration was inhibited. Thus, as seen by the "GDNF+ SW-01" bar in this figure, SW-01 inhibited cell migration induced by activated RET.

Referring to FIGS. 7 and 8, point graphs are shown summarizing the results of xenograft studies (see Example 7 for details). Tumour size in $mm^3$ is plotted versus time in days for subcutaneous tumours derived from human pancreatic cell lines MiaPaca-2 (see FIG. 7) and BxPc3 (see FIG. 8) in nude mice treated with vehicle, SW-01, or gemcitabine. These human pancreatic cell lines were chosen to form the subcutaneous tumours in xenograft animal models as both express RET kinase (see Sawai, H. et al., Cancer Res. (2005) 65: 11536-11544). Xenograft animals are a standard in vivo model to test efficacy and safety of candidate drugs (see representative xenograft studies in Bocci, G. et al., Br. J. Cancer (2005) 93(3): 319-330 and Buchsbaum, D. J. et al., Int. J. Radiat. Oncol. Biol. Phys. (2002) 54(4): 1180-1193). There was no statistical difference between SW-01 and gemcitabine treatment groups (p<0.318) for the MiaPaca-2 studies. As seen in FIG. 8, tumour growth was retarded or stopped by treatment with SW-01. Tumours did not begin to grow rapidly until treatment with SW-01 was discontinued.

Referring to FIGS. 9A and 9B, studies were conducted that probed whether inhibitory effects seen for SW-01 on RET activation were mediated exclusively by SW-01 or were also caused by a derivative of SW-01, norcyclobenzaprine (NCBA or 3-(5H-dibenzo[a,d][7]annulen-5-ylidene)-N-methylpropan-1-amine, available from LGC Standards, Teddington, United Kingdom). NCBA is a metabolite of SW-01. The structural difference is that a certain substituent that is a methyl moiety in SW-01 is a hydrogen in NCBA. It was determined that NCBA inhibited RET. This result is shown in FIG. 9A as a western blot demonstrating that NCBA blocked RET activation by its ligand, GDNF, in a concentration dependent fashion, and in FIG. 9B as a bar graph that indicates reduction in RET phosphorylation with increasing concentrations of NCBA.

Referring to FIGS. 10A, 10B, 11A, and 11B, studies were conducted to determine the effect of SW-01 on mutant forms of RET containing either a valine to methionine change at amino acid 804 (V804M mutant) or a methionine to threonine change at amino acid position 918 (M918T mutant). The M918T mutant form of RET protein occurs in about 50% of sporadic medullary thyroid carcinoma and is the causative mutation in MEN2B, the most aggressive form of that familial cancer syndrome. The V804M mutant form of RET protein occurs in other MEN 2 forms, including MEN 2A and Familial MTC and has been shown to cause those diseases. The V804M mutant forms of RET have been shown to have resistance to RET inhibitors that bind to the RET ATP binding domain (e.g., vandetanib). Without being bound by theory, V804 of RET could act as a "gatekeeper" residue of the kinase, regulating access of ATP to the ATP binding pocket.

In these studies, HEK293 cells, stably expressing RET, were treated with vehicle or indicated concentrations of SW-01 for 2 h. Whole cell lysates were collected and subjected to western blotting for total RET or phosphoRET, as previously described. The results of these studies were that SW-01 inhibits the activity of mutant forms of RET, even cancer causing mutant forms. In FIGS. 10A and 11A for mutant forms of RET V804M and M918T, respectively, images of western blot immunodetection assays are shown demonstrating that cancer causing mutant forms of RET can be inhibited by SW-01 in a concentration dependent fashion.

These results are also shown as bar graphs in FIGS. 10B and 11B. The results indicate that there were decreases in inhibition with increasing concentration of SW-01 in both cases.

Thus, SW-01 inhibits the activity of mutant forms of RET, even cancer causing mutant forms. Accordingly, SW-01 is potentially a useful agent to combat diseases associated with the most aggressive forms of RET mutation, as well as those caused by naturally occurring "resistance mutants" that do not efficiently bind and therefore are not efficiently inhibited by other existing RET inhibitors. The invention includes pharmaceutical compositions and methods employing SW-01 or a salt or analog thereof for treatment of each of the specific cancer types described in the section above entitled "RET and cancer".

TT cells treated with SW-01 for 24 hours exhibited induced morphological changes. These changes were seen under 10× magnification as a less transformed phenotype, i.e., as more rounded cells with less cell-to-cell contact. Higher concentrations of SW-01 resulted in alterations of cell-to-cell and cell-matrix adhesions, indicating possible cell death or growth arrest. Further, RET-expressing cells treated with SW-01 were not able to migrate to close a cell free gap in a wound healing assay (see FIG. 6). A decrease in RET-induced cell proliferation and colony formation was also shown using 3-(4,5-dimethylthiazol-2-yl)-2,5-diphenyltetrazolium bromide (MTT) cell proliferation and soft agar anchorage-independent growth assays, respectively (see FIGS. 3A and B). Inhibition of cell proliferation and colony formation was proportional to the degree of compromise of RET kinase activity.

RET inhibition by SW-01 was studied to determine if it can cause apoptosis. Multiple cell model systems were used to study the effect of SW-01, including embryonic kidney cells (HEK293), medullary thyroid carcinoma cell line (TT), papillary thyroid carcinoma cell line (TPC-1), and neuroblastoma cell line (SKNBE(2)). Using propidium iodide staining and FACS (fluorescence-activated cell sorting) analysis, it was shown that inhibition of RET autophosphorylation by SW-01 led to apoptosis in TT cells, but not in HEK293, TPC-1, and SKNBE(2) cells expressing RET. This result was measured by subG1 population which indicates the percentage of apoptotic cells. This is consistent with the fact that TT cell survival is RET-dependent (Carlomagno, F. et al., J. Nat. Cancer Inst. (2006) 98: 326-334). A decrease in RET-induced colony formation was also shown in soft agar anchorage-independence assays. Together, these data suggests that SW-01 is a significant RET kinase inhibitor.

In accordance with the invention, administration to a subject of a given amount of RET inhibitor results in an effective concentration of the inhibitor in the subject's body. As used herein, the term "effective concentration" is intended to refer to the concentration of RET inhibitor in the subject's body (e.g., in the blood, plasma, or serum, at the target tissue(s), or site(s) of action) capable of producing a desired therapeutic effect. The effective concentration of RET inhibitor in the subject's body may vary among subjects and may fluctuate within a subject over time, depending on factors such as, but not limited to, the condition being treated, genetic profile, metabolic rate, biotransformation capacity, frequency of administration, formulation administered, elimination rate, and rate and/or degree of absorption from the route/site of administration. For at least these reasons, for the purpose of this disclosure, administration of RET inhibitor is conveniently provided as amount or dose of RET inhibitor.

Compositions of the present invention as well as methods described herein for their use may comprise more than one RET inhibitor, formulated and/or administered in various combinations.

The dose of RET inhibitor included in the compositions of the present invention and used in the methodologies described herein is an amount that achieves an effective concentration and/or produces a desired therapeutic effect. For example, such a dosage may be an amount of RET inhibitor well known to the skilled artisan as having a therapeutic action or effect in a subject. Dosages of RET inhibitor producing a desired effect can, for example, typically range between about 0.02 mg/kg to about 100 mg/kg, depending upon, but not limited to, the RET inhibitor selected, the route of administration, the frequency of administration, the formulation administered, and/or the condition being treated. The amounts, dosages, and dose ratios provided herein are exemplary and may be adjusted, using routine procedures such as dose titration, to provide an effective concentration.

For purposes of the present invention, by "therapeutic effect" or "therapeutic activity" or "therapeutic action" it is meant a desired pharmacological activity of a RET inhibitor useful in the inhibition, reduction, suppression, prevention, mitigation or treatment of a tumour or cancer, including prevention, inhibition or reduction of metastasis. In a preferred embodiment, the "therapeutic effect" or "therapeutic activity" or "therapeutic action" is prevention of the spread, and apoptosis of cancer cells.

Accordingly, the compositions of the present invention can be administered to a subject, preferably a mammal, more preferably a human, to treat and/or prevent disease. The compositions may be administered by various routes including, but not limited to, orally, transdermally, dermally, intravenously, intramuscularly, intraperitoneally, topically, subcutaneously, rectally, intraocularly, sublingually, buccally, intranasally or via inhalation. The formulation and route of administration as well as the dose and frequency of administration can be selected routinely by those skilled in the art based upon the severity of the condition being treated, as well as patient-specific factors such as age, weight and the like.

Accordingly, for purposes of the present invention, the therapeutic compound, namely the RET inhibitor, can be administered in a pharmaceutically acceptable vehicle.

As used herein "pharmaceutically acceptable vehicle" includes any and all solvents, excipients, dispersion media, coatings, antibacterial and antifungal agents, isotonic and absorption delaying agents, and the like which are compatible with the activity of the therapeutic compound and are physiologically acceptable to a subject. An example of a pharmaceutically acceptable vehicle is buffered normal saline (0.15 M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

Carrier or substituent moieties useful in the present invention may also include moieties which allow the therapeutic compound to be selectively delivered to a target organ. For example, delivery of the therapeutic compound to a tumour may be enhanced by a carrier moiety using either active or passive transport (a "targeting moiety"). Illustratively, the carrier molecule may be a redox moiety, as described in, for example, U.S. Pat. Nos. 4,540,654 and 5,389,623, both to Bodor. These patents disclose drugs linked to dihydropyridine moieties which can enter the brain, where they are oxidized to a charged pyridinium species which is trapped in the brain. Thus drugs linked to these moieties accumulate in the brain. Other carrier moieties include compounds, such as amino acids or thyroxine, which can be passively or actively transported in vivo. Such a carrier moiety can be metabolically removed in vivo, or can remain intact as part of an active compound.

Structural mimics of amino acids (and other actively transported moieties) including peptidomimetics, are also useful in the invention. As used herein, the term "peptidomimetic" is intended to include peptide analogues which serve as appropriate substitutes for peptides in interactions with, for example, receptors and enzymes. The peptidomimetic must possess not only affinity, but also efficacy and substrate function. That is, a peptidomimetic exhibits functions of a peptide, without restriction of structure to amino acid constituents. Peptidomimetics, methods for their preparation and use are described in Morgan et al. (1989) ("Approaches to the discovery of non-peptide ligands for peptide receptors and peptidases," In *Annual Reports in Medicinal Chemistry* (Virick, F. J., ed.), Academic Press, San Diego, Calif., pp. 243-253), the contents of which are incorporated herein by reference. Many targeting moieties are known, and include, for example, asialoglycoproteins (see e.g., Wu, U.S. Pat. No. 5,166,320) and other ligands which are transported into cells via receptor-mediated endocytosis (see below for further examples of targeting moieties which may be covalently or non-covalently bound to a target molecule).

The term "subject" as used herein is intended to include living organisms in which cancer to be treated can occur. Examples of subjects include mammals such as humans, apes, monkeys, cows, sheep, goats, dogs, cats, mice, rats, and transgenic species thereof. As would be apparent to a person of skill in the art, the animal subjects employed in the working examples set forth below are reasonable models for human subjects with respect to the tissues and biochemical pathways in question, and consequently the methods, therapeutic compounds and pharmaceutical compositions directed to same. As evidenced by Mordenti (*J. Pharm. Sci.* (1986) 75(11): 1028-40) and similar articles, dosage forms for animals such as, for example, rats can be and are widely used directly to establish dosage levels in therapeutic applications in higher mammals, including humans. In particular, the biochemical cascade initiated by many physiological processes and conditions is generally accepted to be identical in mammalian species (see, e.g., Mattson et al. *Neurotrauma* (1994) 11(1): 3-33; Higashi et al. *Neuropathol. Appl. Neurobiol.* (1995) 21:480-483). In light of this, pharmacological agents that are efficacious in animal models such as those described herein are believed to be predictive of clinical efficacy in humans, after appropriate adjustment of dosage.

Depending on the route of administration, the therapeutic compound may be coated in a material to protect the compound from the action of acids, enzymes and other natural conditions which may inactivate the compound.

The invention also provides a combination therapy in which two or more therapeutic compounds are administered. Each of the therapeutic compounds may be administered by the same route or by a different route. Also, the compounds may be administered either at the same time (i.e., simultaneously) or each at different times. In some treatment regimes it may be beneficial to administer one of the compounds more or less frequently than the other.

In some embodiments of combination therapy, a first compound is of Formula (1A), (1B) or (1C), and a second, different compound is also of Formula (1A), (1B) or (1C). In other embodiments, the second compound is an antineoplastic agent that is not of Formula (1A), (1B) or (1C). Known antineoplastic agents that may be suitable in a combination therapy according to the invention include, but are not limited to anthracyclines (e.g., doxorubicin, daunorubicin), other antibiotic agents (e.g, the HSP90 inhibitor 17-AAG), Vinca alkaloids (e.g., vinblastine, vincristine), epipodophyllotoxins (e.g., etoposide, teniposide), pyrimidine analogs (e.g., gemcitabine, 5-fluorouracil, cytarabine), taxanes (e.g., paclitaxel), platinum-based cancer drugs (e.g., cisplatin), monoclonal antibodies (e.g., Herceptin), and equivalents thereof.

The compounds of the invention can be formulated to ensure proper distribution in vivo. For example, therapeutic compounds of the invention can be formulated in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., Ranade, V. V. J. Clin. Pharmacol. (1989) 29(8):685-94). Exemplary targeting moieties include folate and biotin (see, e.g., U.S. Pat. No. 5,416,016 to Low et al.); mannosides (Umezawa et al., *Biochem. Biophys. Res. Commun.* (1988) 153(3):1038-44; antibodies (Bloeman et al., *FEBS Lett.* (1995) 357:140; Owais et al., *Antimicrob. Agents Chemother.* (1995) 39(1):180-4); and surfactant protein A receptor (Briscoe et al., *Am. J. Physiol.* (1995) 268(3 Pt 1): L374-80). Liposomal formulations of RET inhibitors may include a targeting moiety.

Delivery and in vivo distribution can also be affected by alteration of an anionic group of compounds of the invention. For example, anionic groups such as phosphonate or carboxylate can be esterified to provide compounds with desirable pharmacokinetic, pharmacodynamic, biodistributive, or other properties.

To administer a therapeutic compound by other than parenteral administration, it may be necessary to coat the compound with, or co-administer the compound with, a material to prevent its inactivation. For example, the therapeutic compound may be administered to a subject in an appropriate vehicle, for example, liposomes, or a diluent. Pharmaceutically acceptable diluents include saline and aqueous buffer solutions. Liposomes include water-in-oil-in-water CGF emulsions as well as conventional liposomes (Strejan et al., *Prog. Clin. Biol. Res.* (1984) 146: 429-34).

The therapeutic compound may also be administered parenterally (e.g., intramuscularly, intravenously, intraperitoneally, intraspinally, intrathecally, or intracerebrally). Dispersions can be prepared in glycerol, liquid polyethylene glycols, and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g. vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

Solid dosage forms for oral administration include ingestible capsules, tablets, pills, lollipops, powders, granules, elixirs, suspensions, syrups, wafers, buccal tablets, troches, and the like. In such solid dosage forms the active compound is mixed with at least one inert, pharmaceutically acceptable excipient or diluent or assimilable edible vehicle such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the therapeutic compound in the compositions and preparations may, of course, be varied. The amount of the therapeutic compound in such therapeutically useful compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Therapeutic compounds can be administered in time-release or depot form, to obtain sustained release of the therapeutic compounds over time. The therapeutic compounds of the invention can also be administered transdermally (e.g., by providing the therapeutic compound, with a suitable vehicle, in patch form).

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of neurological conditions in subjects.

Therapeutic compounds according to the invention are administered at a therapeutically effective dosage sufficient to achieve the desired therapeutic effect of the RET inhibitor, e.g. to prevent the spread of cancer and/or kill cancerous cells. Actual dosage levels of active ingredients in the pharmaceutical compositions of this invention may be varied so as to obtain an amount of the active compound(s) that is effective to achieve and maintain the desired therapeutic response for a particular subject, composition, and mode of administration. The selected dosage level will depend upon the activity of the particular compound, the route of administration, frequency of administration, the severity of the condition being treated, the condition and prior medical history of the subject being treated, the age, sex, weight and genetic profile of the subject, and the ability of the therapeutic compound to produce the desired therapeutic effect in the subject. Dosage regimens can be adjusted to provide the optimum therapeutic response. For example, several divided doses may be administered daily or the dose may be proportionally reduced as indicated by the exigencies of the therapeutic situation.

However, it is well known within the medical art to determine the proper dose for a particular patient by the dose titration method. In this method, the patient is started with a dose of the drug compound at a level lower than that required to achieve the desired therapeutic effect. The dose is then gradually increased until the desired effect is achieved. Starting dosage levels for an already commercially available therapeutic agent of the classes discussed above can be derived from the information already available on the dosages employed. Also, dosages are routinely determined through preclinical ADME toxicology studies and subsequent clinical trials as required by the FDA or equivalent agency. The ability of a RET inhibitor to produce the desired therapeutic effect may be demonstrated in various well known models for the various conditions treated with these therapeutic compounds.

"Bioisosterism" is a lead modification approach used by those skilled in the art of drug design and shown to be useful in attenuating toxicity and modifying activity of a lead compound. Bioisosteric approaches are discussed in detail in standard reference texts such as The Organic Chemistry of Drug Design and Drug Action (Silverman, R B, Academic Press, Inc. 1992 San Diego, Calif., pages 19-23). Classical "bioisosteres" comprise chemical groups with the same number of valence electrons but which may have a different number of atoms. Thus, for example, classical bioisosteres with univalent atoms and groups include, but are not limited to: $CH_3$, $NH_2$, OH, F and Cl; Cl, $PH_2$ and SH; Br and i-Pr; and I and t-Bu. Classical bioisosteres with bivalent atoms and groups include, but are not limited to: —$CH_2$— and NH; O, S, and Se; and $COCH_2$, CONHR, $CO_2R$ and COSR. Classical bioisosteres with trivalent atoms and groups include, but are not limited to: CH= and N=; and P= and As=. Classical bioisosteres with tetravalent atoms include, but are not limited to: C and Si; and =$C^+$=, =$N^+$= and =$P^+$=. Classical bioisosteres with ring equivalents include, but are not limited to: benzene and thiophene; benzene and pyridine; and tetrahydrofuran, tetrahydrothiophene, cyclopentane and pyrrolidine. Nonclassical bioisosteres still produce a similar biological activity, but do not have the same number of atoms and do not fit the electronic and steric rules of classical isosteres. Exemplary nonclassical bioisoteres are shown in the following table.

Nonclassical Biosteres:

1. Carbonyl group

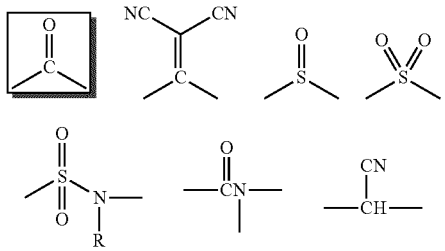

2. Carboxylic acid group

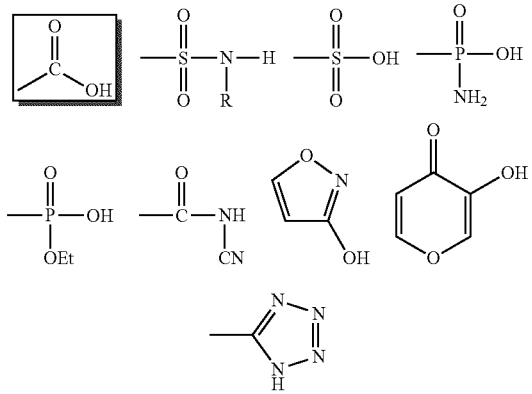

3. Hydroxy group

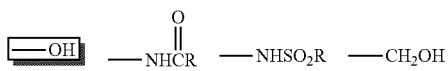

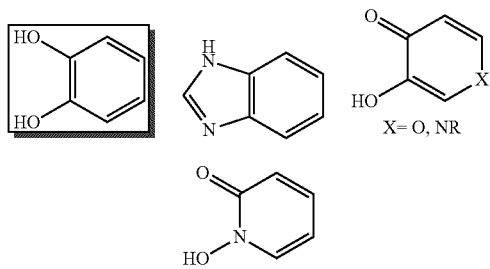

4. Catachol

5. Halogen

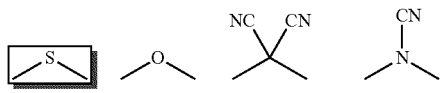

6. Thioether

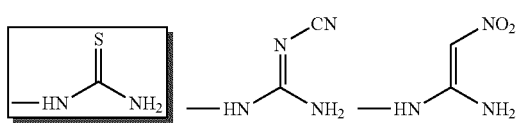

7. Thiourea

8. Azomethine

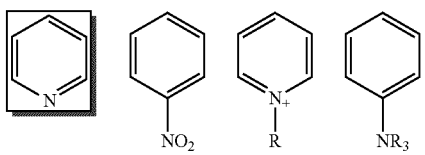

9. Pyridine

10. Spacer group

11. Hydrogen

H  F

Additional bioisosteric interchanges useful in the design of small organic molecule mimetics of the present invention include ring-chain transformations.

The following nonlimiting examples are provided to further illustrate the present invention.

WORKING EXAMPLES

Example 1

Experimental Methods

Example 1A

Inhibitor Compounds

Inhibitor compounds NSC1077, NSC27476, NSC78206 (SW-01), SW-02, SW-03, SW-04, and SW-05 were received from a structural diversity set of the Drug Synthesis and Chemistry Branch, Developmental Therapeutics Program, Division of Cancer Treatment and Diagnosis (NCI/NIH, USA see http://dtp.nci.nih.gov/). Compounds that were commercially available for purchase included SW-06 and SW-07 (available from Tocris Bioscience Ltd., Ellisville, Mo., USA), SW-08 (available from Fisher Scientific, Pittsburgh, Pa., USA), SW-09 (available from Sigma-Aldrich, Oakville, ON, Canada), SW-11, SW-12 and SW-13 (available from Interchim, Montlucon, France). It should be noted that compounds SW-02 and SW-04 differ in that SW-04 is the free base form and SW-02 is the hydrochloride salt form. In buffered media these compounds are expected to be the same.

Example 1B

Cell Culture and Transfection

TT, MiaPaca-2, MCF-7 were received from the American Type Culture Collection, (Manassas, Va.) and grown in Dulbecco's Modified Eagle's Medium (DMEM) (Invitrogen, Burlington, ON, Canada) supplemented with 10% fetal bovine serum (Sigma, Oakville, ON, Canada). HEK293 cells expressing the reverse-tetracycline transcriptional activator (Tet-on) were received from BD Biosciences (Mississauga, ON, Canada) and grown in DMEM (Invitrogen, Burlington, ON, Canada) supplemented with 10% fetal bovine serum (Sigma, Oakville, ON, Canada) and 1 µg/mL doxycycline. In the latter cells, 1 µM AP20187 dimerizer (ARIAD, Cambridge, Mass.) was added to induce intracellular RET dimerization 30 minutes before harvesting.

Example 1C

Immunoprecipitations and Western Blotting

Total protein lysates were harvested 48 hours after transfection and suspended in 20 mM Tris-HCl (pH 7.8), 150 mM NaCl, 1 mM sodium orthovanadate, 1% Igepal, 2 mM EDTA, 1 mM PMSF, 10 µg/ml aprotonin, and 10 µg/ml leupeptin (see Myers, S. M. et al., *Cancer Res.* (2004) 64: 4453-4463). Protein assays were carried out using the BCA protein assay kit received from Pierce (Rockford, Ill., USA).

RET expression was detected using the C-19 antibody received from Santa Cruz Biotechnology (Santa Cruz, Calif., USA) and RET tyrosine phosphorylation was detected using an anti-pRET antibody received from Cell Signaling (Beverly, Mass., USA) that specifically recognizes phosphorylation of primary tyrosine residue Y905 (see Kawamoto, Y. et al., *J. Biol. Chem.* (2004) 279: 14213-14224). For immunoprecipitations, lysates were incubated with a 1:50 dilution of the appropriate primary antibody with agitation for 2 hours at 4° C., mixed with Protein AG (Santa Cruz Biotechnology) and incubated on ice for 2 hours, with shaking. Immunoprecipitates were pelleted, washed, and resuspended in SDS-PAGE sample buffer. Samples were denatured, separated on 10% SDS-PAGE gels and transferred to nitrocellulose membranes received from Bio-Rad (Mississauga, ON, Canada).

Example 1D

Protein Based RET Kinase Assay

Approximately 5-20 µg of purified GST-RET proteins were incubated with 1 mM ATP in 20 µL kinase buffer (10 mM Tris-HCl, 5 mM $MgCl_2$, pH 7.4), at 30° C. for 30 minutes. The kinase reactions were terminated by boiling the samples in SDS-PAGE sample buffer. Samples were resolved on 10% acrylamide gels by SDS-PAGE followed by Western blotting. Phosphorylation was detected using a pan-phosphotyrosine pY99 antibody (available from Santa Cruz Biotechnology) or RET phospho-specific antibody (pY905, available from Cell Signaling, Beverly, Mass., USA).

Example 1E

MTT Cell Proliferation Assay

MTT (3-(4,5-dimethylthiazol-2-yl)-2,5-diphenyltetrazolium bromide) cell viability assays were performed according to the method described in Mosmann, T., *J. Immunol. Methods*, 65: 55-63 (1983). Briefly, HEK293 cells stably expressing RET were seeded in 6-well plates. One half of the cells expressing RET were treated with inhibitors for the time period indicated. All cells were subsequently treated with 100 ng/mL GDNF and seeded into 96 well plates 24 hours post transfection. After 3 days of incubation under normal culture conditions, MTT was added at a final concentration of 250 µg/mL (0.6 mM) and incubated for another 2 h at 37° C. The mitochondria of viable cells can reduce MTT to formazan, which was dissolved with 150 µL DMSO. Reduced MTT was then measured spectrophotometrically in a microtiter plate reader at 570 nm. The statistical significance was calculated by one-way ANOVA.

Example 1F

Flow Cytometry

Cells were cultured, and treated with DMSO or test compounds solubilized in DMSO for a certain time period (as indicated). After several washes with phosphate buffered saline (PBS), cells were harvested, and $1-2\times10^6$ cells were resuspended in 1 mL of PBS. The cells were then fixed in absolute ethanol, treated with 20 µL RNaseA and incubated at 37° C. overnight. Propidium iodide (100 µg) was then added, and samples were incubated for 15 minutes at room temperature. Cell cycle analysis was then performed using an EPICS ALTRA HSS flow cytometer (Beckman Coulter, Mississauga, ON, Canada). The statistical significance was calculated by one-way ANOVA.

Example 1G

Soft Agar Colony Formation Assay

Soft agar colony formation assays were done as described previously (see Gujral et al. *Cancer Res* (2006) 66: 10741-10749). Briefly, approximately $5\times10^4$ RET-expressing HEK293 cells were resuspended in 0.2% top agar in medium, and plated on 0.4% bottom agar in medium supplemented with GDNF and containing DMSO or the indicated concentration of inhibitors. Culture medium was replenished or changed every 2 to 3 days. Colonies were counted after 2 weeks, and statistical significance was confirmed by one-way ANOVA.

Example 2

Studies of Autophosphorylation of RET in the Presence of SW-01

TET-ON HEK293 cells stably expressing RET were grown to 70% confluence and RET expression was induced with 1 µg/mL doxycycline. SW-01 or another test compound was added 2 hours before harvesting. In addition, 1 µM AP20187 dimerizer (ARIAD, Cambridge, Mass.) was added to induce icRET dimerization 30 minutes before harvesting. Protein assays were performed as described above. Whole cell lysates were subjected to Western blotting using anti-phosphoRET (pY905) antibody to assess phosphorylation of RET and pan RET antibody (anti RET C-19) to assess the total amount of RET.

Example 2A

Effect of Test Compounds on Autophosphorylation of RET

HEK293 cells, stably expressing activated wildtype RET, were treated with DMSO or test compounds solubilized in DMSO, to final concentrations of 10 µM for 2 hours. The cells were harvested, resolved on 10% SDS-PAGE and immunoblotted with anti-phosphoRET or pan RET antibodies, as indicated in FIG. 2A. Results of the tests can be seen in FIG. 2A; as shown, SW-01 significantly inhibited RET autophosphorylation.

Example 2B

Using a Recombinant Protein Kinase Assay to Study RET Inhibition

Protein based kinase kinetics: Approximately 5-20 µg of purified GST-RET proteins were incubated with 1 mM ATP in 20 µL kinase buffer (10 mM Tris-HCl, 5 mM $MgCl_2$, pH 7.4) at 30° C. for 30 minutes. Kinase reactions were terminated by boiling samples in SDS-PAGE sample buffer (20 mM Tris-HCl, pH 7.8, 150 mM NaCl, 1 mM sodium orthovanadate, 1% Igepal, 2 mM EDTA, 1 mM PMSF, 10 µg/mL aprotonin, and 10 µg/mL leupeptin). Samples were resolved on 10% acrylamide gels by SDS-PAGE followed by Western blotting. Phosphorylation was detected using a pan-phosphotyrosine (pY99) antibody or RET phospho-specific antibody (pY905) (Cell Signaling, Beverly, Mass., USA). The pY905 phospho-RET antibody recognizes phosphorylation of RET at residue Y905 which is a primary phosphotyrosine which lies in the activation loop of the kinase.

Blots were re-probed with pan RET antibody to detect the total amount of RET protein. Results of this recombinant protein kinase assay test are depicted in FIG. 2B. It was determined that SW-01 significantly reduced RET autokinase activity.

Example 2C

Using Cell-Based Assays to Study Effect of SW-01 on RET Autophosphorylation

To further study its inhibition of RET autophosphorylation, SW-01 was tested in cell based assays in which HEK293 cells that over-express wild type RET were used. The cells were treated with varying concentrations of SW-01 for 2 hours. RET phosphorylation was blocked or dramatically reduced upon SW-01 treatment in a concentration-dependent manner (see FIG. 2C). Also as shown, SW-01 did not affect expression levels of RET. SW-01 was thus identified as a RET inhibitor which blocks autokinase activity in a cell based assay.

Example 2D

Effect of SW-01 on RET-Mediated Downstream Signaling, Cellular Growth, Proliferation and Transformation Upon activation, RET transduces downstream signals through phosphorylation of multiple intracellular tyrosines. It has been shown to activate many signaling pathways including RAS-ERK, which was selected for study. Whole cell lysates from HEK293 cells were treated with increasing concentrations of SW-01. Treated lysates were resolved using SDS-PAGE and immunoblotted with antibodies against RET, ERK, and phosphorylated ERK ("pERK"). As shown in FIG. 2D, the amount of pERK is significantly reduced with increasing concentration of SW-01, while the amounts of RET and ERK remain the same. Thus, it was shown by this study that SW-01 blocks RET-mediated activation of ERK without affecting its expression levels.

Example 3A

Effect of SW-01 on Cell Proliferation Measured by MTT Assay

HEK293 cells stably expressing RET were treated with SW-01 or DMSO, and cell proliferation was measured by MTT assay. Results are shown as mean values of at least 3 replicates with standard deviation in FIG. 3A. In summary, SW-01 reduces RET-mediated cell proliferation in HEK293 cells.

Example 3B

Effect of SW-01 on Colony Formation in Soft Agar

A study was conducted to determine effects of SW-01 concentration on relative colony formation in a soft agar cell growth assay in HEK293 cells. In summary, SW-01 inhibits RET-mediated colony formation in the soft agar assay. Results are shown in FIG. 3B wherein colony formation is expressed as relative mean colony number compared to vehicle control with standard deviation for a minimum of three replicate experiments.

Example 3C

Effect of SW-01 on Apoptosis

Multiple cell model systems including embryonic kidney cells (HEK293), thyroid cancer cells (TT) and neuronal SKNBE(2) cells, were used to study the effect of SW-01 on apoptosis. This was measured by determining subG1 population via propidium iodide staining and flow cytometry analysis which indicates the percentage of apoptotic cells. Results are depicted in FIG. 3C. Inhibition of RET autophosphorylation by SW-01 led to apoptosis in TT cells, but not in HEK293, and SKNBE(2) cells expressing RET. This is consistent with the fact that TT cell survival is RET-dependent (Carlomagno, F. et al., *J. Nat. Cancer Inst.* (2006) 98: 326-334).

Example 4

Effect of SW-01 and Analogs on RET Autophosphorylation

Four structurally similar analogs of SW-01 were tested to determine their effect on RET autophosphorylation. HEK293 cells stably expressing activated RET were treated with test compounds or vehicle (DMSO). Cells were harvested and subjected to Western blotting. Autokinase activity of RET was evaluated using a phosphoRET antibody, pY905. Blots were reprobed with a pan RET antibody to detect amounts of RET proteins. Two of the test compounds, SW-03 and SW-04, did not affect RET autophosphorylation while SW-02 and SW-05 decreased RET activity. Results are shown in FIG. 4, where chemical structures of the test compounds, images of the Western blots, and bar graphs of the pRET/RET ratios versus concentration of specified test compound, are shown.

Example 5

Flow Cytometry Studies of Effect of SW-01 on Various Cancer Cell Lines

In flow cytometry studies, cells were cultured, and treated with DMSO or inhibitors for a specified time period. After several washes with PBS, cells were harvested and $1\text{-}2 \times 10^6$ cells were resuspended in 1 mL of PBS. The cells were then fixed in absolute ethanol, treated with 20 μL RNaseA and incubated at 37° C. overnight. Then 100 μg propidium iodide was added, and samples were incubated for 15 minutes at room temperature. Cell cycle analysis was performed using an EPICS ALTRA HSS flow cytometer (Beckman Coulter, Mississauga, ON, Canada).

Example 5A

Flow cytometry (see experimental details above) was used to study the effect of SW-01 on apoptosis in a pancreatic cancer cell line (MiaPaca-2) in the presence of GDNF. Treatment with SW-01 caused dose-dependent apoptosis in Mia-Paca-2 cells as shown in FIG. 5A. GDNF was necessary for RET activation. SW-01 inhibited RET activation and induced cell death in the presence of GDNF.

Example 5B

A MTT cell proliferation assay was performed in pancreatic cancer cell lines (MiaPaca-2 and BxPc3) generating inhibition curves showing percentage cell growth versus SW-01 concentrations. Treatment with SW-01 caused decreased cell proliferation in both MiaPaca-2 and BxPc3 cell lines. The inhibition curves and $EC_{50}$ values of SW-01 in each cell line are indicated in FIG. 5B.

Example 5C

A MTT cell proliferation assay was performed in a pancreatic cancer cell line (MiaPaca-2) generating inhibition curves showing percentage cell growth versus concentration of SW-01, gemcitabine, or both in combination. The inhibition curves and $EC_{50}$ values of each treatment are indicated in FIG. 5C.

Example 5D

Flow cytometry (see experimental details above) was used to study the effect of SW-01 on apoptosis in a lung cancer cell line (NCIH69) in the presence and absence of GDNF. Treatment with SW-01 caused apoptosis in NCIH69 cells in a dose-dependent fashion, as shown in FIG. 5D.

Example 5E

Flow cytometry (see experimental details above) was used to study the effect of SW-01 on apoptosis in a breast cancer cell line (MCF7) in the presence of GDNF. Treatment with SW-01 caused apoptosis in MCF7 cells in a dose-dependent fashion, as shown in FIG. 5E.

Example 6

Wound Area Study of SW-01

A study was conducted to determine SW-01's effect on wound healing over time in MiaPaca-2 pancreatic cancer cell line expressing RET in the presence or absence of GDNF and in the presence or absence of GDNF and SW-01. Results are shown in FIG. 6. Wound diameter means area of wound space remaining after time. The results indicate that cell migration was inhibited in the presence of GDNF and SW-01 relative to cell migration in the presence of GDNF alone.

Example 7

Xenograft Studies

Xenograft studies were selected to test the efficacy of SW-01 in vivo. These studies were performed by Washington Biotechnology, Inc. of Simpsonville, Md., U.S.A. In these studies pancreatic cancer cell lines MiaPaca-2 and BxPc3 (American Type Culture Collection (ATCC), Manassas, Va., USA) were used to create the tumours in vivo. When their tumours reached 100 mm³ in size, the mice were treated with either vehicle, SW-01 (50 mg/kg in vehicle), or gemcitabine (120 mg/kg in vehicle) by intraperitoneal injection every three days for four doses. The growth of the tumours was monitored over time. Details of these studies are provided below.

Cells were thawed out and dispersed into a 75 cm² flask containing: Dulbecco's Modified Eagle's Medium supplemented with 10% fetal bovine serum and 2.5% horse serum (for the MiaPaca-2 cells) and RPMI-1640 Medium supplemented with 10% fetal bovine serum (for the BxPc3 cells). Cells were incubated at 37° C. in humidified atmosphere of 5% $CO_2$ and media were supplemented or renewed as needed. Cell cultures were expanded until there were 800 million cells available for injection into mice for xenograft studies.

Male athymic nude mice (5-6 weeks old) were housed in filter-topped cages supplied with autoclaved bedding. All mouse handling procedures were conducted under a laminar flow hood. The weights of the mice were recorded and they were ear tagged for individual identification. Mice were injected subcutaneously in each flank with 10 million cells of either MiaPaca-2 or BxPc3 cells in 0.1 mL of sterile phosphate-buffered saline solution. Tumour measurements were recorded every Monday, Wednesday, and Friday until tumour volume were approximately 80-120 mm³ (sum of tumours on both flanks). Tumour sizes and individual animal weights were measured by a single technician to reduce variability.

Mice were sorted into treatment groups with seven mice per group in the MiaPaca-2 studies and eight mice per group for the BxPc3 studies with a control group of five mice for each study. Selection was based upon tumour sizes so each group had a similar mean tumour volume and a similar spread of tumour size. The mice were dosed intraperitoneally every three days for six treatments in a volume of 10 mL/kg. The mice were injected with either vehicle (saline), SW-01 (Sigma-Aldrich) (50 mg/kg in saline), or gemcitabine (Carbosynth Limited, Compton, Berkshire, UK) (120 mg/kg in saline) as indicated in FIGS. 7 and 8. Tumour volumes and animal weights were measured every Monday, Wednesday, and Friday for thirty days total for the MiaPaca-2 studies, and for sixty-eight days total for the BxPc3 studies. The BxPc3 xenograft grew more slowly than the MiaPaca-2 xenograft.

In both studies, animal weight between the groups was maintained and there was no statistical difference for this variable. There was no statistical difference between SW-01 and gemcitabine treatment groups (p<0.318) for the MiaPaca-2 studies. As seen in FIG. 8, SW-01 caused slowed and reduced tumour growth in the BxPc3 tumours; only after the last dosing did the tumour begin to grow once again.

Example 8

Studies of Norcyclobenzaprine (NCBA) and its Inhibition of Autophosphorylation of RET This study probed whether inhibitory effects seen for SW-01 on RET activation were mediated exclusively by SW-01 or were also caused by a derivative of SW-01, norcyclobenzaprine (NCBA). NCBA is a metabolite of SW-01 in which a methyl substituent in SW-01 is a hydrogen substitutent in NCBA. It was determined that NCBA inhibited RET as shown in FIGS. 9A and 9B.

FIG. 9A shows images of a western blot assay demonstrating that NCBA blocked RET activation by its ligand, GDNF, in a concentration dependent fashion. HEK293 cells, stably expressing RET, were treated with vehicle or indicated concentrations of NCBA for 2 h. Whole cell lysates were collected and subjected to western blotting for total RET or phosphoRET, as previously described. In FIG. 9B, results of these studies are presented as a bar graph that indicates reduction in RET phosphorylation with increasing concentrations of NCBA.

Example 9

Inhibition of Phosphorylation of RET Mutants by SW-01

This study evaluated the effect of SW-01 on mutant forms of RET containing either a methionine to threonine change at amino acid position 918 (M918T mutant), or a valine to methionine change at amino acid 804 (V804M mutant). In these studies, HEK293 cells stably expressing RET were treated with vehicle or indicated concentrations of SW-01 for 2 h. Whole cell lysates were collected and subjected to western blotting for total RET (panRET antibody) or phospho-RET (anti-pRET antibody), as previously described.

In FIGS. 10A and 11A for V804M and M918T, respectively, images of western blot immunodetection assays are shown demonstrating that cancer causing mutant forms of RET can be inhibited by SW-01 in a concentration dependent fashion. These results are also shown as bar graphs in FIGS. 10B and 11B. The results indicate that there was a relative decrease in inhibition with increasing concentration of SW-01.

All publications listed and cited herein are incorporated herein by reference in their entirety. It will be understood by those skilled in the art that this description is made with reference to certain preferred embodiments and that it is possible to make other embodiments employing the principles of the invention which fall within its spirit and scope as defined by the claims.

TABLE 1

Effect of SW-01 on inhibition of various receptor and non receptor tyrosine and serine/threonine kinases

| Protein | SW-01 Inhibition (10 μM) |
|---|---|
| RET | ++ |
| Met | -- |
| c-KIT | -- |
| FPS/FER | -- |
| SRC | -- |
| AKT | -- |
| ERK | -- |
| MEK1/2 | -- |

++ inhibition was detected via phosphorylation levels;
-- no change in the phosphorylation levels was detected

TABLE 2

Relative expression of RET in small cell and non small cell lung carcinoma cell lines

| Cell Line | Type | RET expression |
|---|---|---|
| A549 | NSCLC | -- |
| SHP-77 | SCLC | ++ |
| NCIH69 | NSCLC | + |

++ high expression of RET was detected;
+ moderate expression of RET was detected;
-- low or no expression of RET was detected

TABLE 3

Name, structure, median inhibitory concentration ($IC_{50}$) in purified protein assays and median effective concentration ($EC_{50}$) in cell based assays of test compounds

| Compound | Chemical Name Chemical Abstracts Service (CAS) number | Chemical Struture | $IC_{50}$ (μM) | $EC_{50}$ (μM) |
|---|---|---|---|---|
| SW-01 | Cyclobenzaprine Hydrochloride CAS 303-53-7 | | 0.3 | 1 |
| SW-05 | Amitriptyline CAS 50-48-6 | | 1 | 5 |
| SW-04 | Nortriptyline CAS 72-69-5 | | 1.5 | 10 |
| SW-13 | [2-(5H-Dibenzo[a,d]cyclohepten-5-yloxy)-ethyl]-dimethyl-amine CAS 2521-76-8 | | 2.5 | 7 |

TABLE 3-continued

Name, structure, median inhibitory concentration ($IC_{50}$) in purified protein assays and median effective concentration ($EC_{50}$) in cell based assays of test compounds

| Compound | Chemical Name Chemical Abstracts Service (CAS) number | Chemical Struture | $IC_{50}$ (μM) | $EC_{50}$ (μM) |
|---|---|---|---|---|
| SW-12 | (5H-Dibenzo[a,d]cyclohepten-5-yl)-acetic acid 3-diethylamino-propyl ester CAS 5093-07-2 | | 4 | >20 |
| SW-08 | 10,11-Dihydro-5H-dibenzo[a,d]cycloheptene-5-methanamine CAS 7351-49-7 | | 5 | 20 |
| SW-02 | Nortriptyline Hydrochloride CAS 894-71-3 | | 5 | >20 |
| SW-03 | 3-(10,11-Dihydro-5H-dibenzo[a,d]cyclohepten-5-ylidene)-N,N-dimethyl-1-propanamine N-oxide hydrochloride CAS 4290-60-2 | | 10 | >20 |
| SW-11 | 5-(3-Dimethylamino-propyl)-5H-dibenzo[a,d]cyclohepten-5-ol CAS 18029-54-4 | | >10 | >20 |
| SW-06 | Lofepramine CAS 23047-25-8 | | >20 | >20 |
| SW-07 | Doxepin Hydrochloride CAS 1229-29-4 | | >20 | >10 |

TABLE 3-continued

Name, structure, median inhibitory concentration ($IC_{50}$) in purified protein assays and median effective concentration ($EC_{50}$) in cell based assays of test compounds

| Compound | Chemical Name Chemical Abstracts Service (CAS) number | Chemical Struture | $IC_{50}$ (µM) | $EC_{50}$ (µM) |
|---|---|---|---|---|
| SW-09 | N'-Fluoren-9-yl-N,N-dimethyl-ethylenediamine dihydrochloride CAS 20799-95-5 | | >20 | >20 |
| SW-10 | 9,9-Bis(3-aminopropyl)-fluorine CAS 2409-19-0 | | >20 | >20 |
| SW-14 | Melitracin CAS 10563-70-9 | | >20 | >20 |
| SW-15 | Norcyclo-benzaprine (NCBA) CAS 303-50-4 | | N/A | 1 |

We claim:

1. A method of treating and/or mitigating cancer, comprising administering to a subject gemcitabine and a compound of Formula (1B):

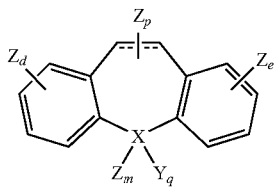

where

X is $sp^2$ hybridized carbon, $sp^3$ hybridized carbon, or $sp^3$ hybridized nitrogen;

Y is $sp^2$ hybridized carbon bonded to a non-cyclic aliphatic group optionally comprising one or more heteroatoms;

$R^4$ and $R^5$ are independently H or alkyl;

$R^6$ and $R^7$ are independently alkyl;

Z is independently H, aryl, halo, nitro, hydroxyl, amino, thiol, alkoxyl, amido, amide, carboxyl, alkenyl, allyl, cyano, substituted alkyl, alkylamino, halogenated alkyl, or unsubstituted alkyl;

d is 0-7; e is 0-7; m is 0; p is 0-2; q is 1; and dotted line indicates that the compound may be saturated or unsaturated at that location;

where the cancer is a cancer associated with expression of REarranged during Transfection protooncogene ("RET") selected from the group consisting of medullary thyroid carcinoma, papillary thyroid carcinoma, pheochromocytoma, multiple endocrine neoplasia type 2 related tumor, testicular cancer, and pancreatic cancer; and where the amount of compound (1B) administered corresponds to between about 0.02 mg/kg to about 100 mg/kg in the subject.

2. The method of claim 1, wherein the compound of Formula (1B) as defined in claim 1 inhibits RET kinase activity.

3. The method of claim 1, wherein X comprises $sp^2$ hybridized carbon.

4. The method of claim 1, wherein d and e are each 0.

5. The method of claim 1, wherein the compound of Formula (1B) is cyclobenzaprine (SW-01).

6. A method of inhibiting RET kinase activity comprising contacting RET protein with a compound of Formula (1B) as defined in claim 1.

7. The method of claim 6, wherein the contacting is in solution.

8. The method of claim 6, wherein the contacting is in cell culture.

9. The method of claim 6, wherein the contacting is in a subject.

10. The method of claim 1, wherein the amount of compound (1B) corresponds to between about 0.02 mg/kg to about 100 mg/kg in a patient in need thereof.

11. The method of claim 10, wherein the administering is parenteral or intravenous administering.

12. A pharmaceutical composition for the treatment and/or mitigation of cancer, comprising effective amounts of gemcitabine and a compound of Formula (1B):

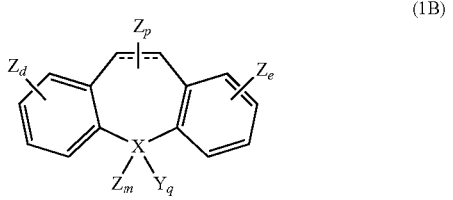

(1B)

where X is sp² hybridized carbon, sp³ hybridized carbon, or sp³ hybridized nitrogen;
Y is sp² hybridized carbon bonded to a non-cyclic aliphatic group optionally comprising one or more heteroatoms;
$R^4$ and $R^5$ are independently H or alkyl;
$R^6$ and $R^7$ are independently alkyl;
Z is independently H, aryl, halo, nitro, hydroxyl, amino, thiol, alkoxyl, amido, amide, carboxyl, alkenyl, allyl, cyano, substituted alkyl, alkylamino, halogenated alkyl, or unsubstituted alkyl;
d is 0-7; e is 0-7; m is 0; p is 0-2; and q is 1; and
dotted line indicates that the compound may be saturated or unsaturated at that location;
wherein the compound of Formula (1B) inhibits RET kinase activity and the cancer is a cancer associated with expression of RET selected from the group consisting of medullary thyroid carcinoma, papillary thyroid carcinoma, pheochromocytoma, multiple endocrine neoplasia type 2 related tumor, testicular cancer, and pancreatic cancer and
where the amount of compound (1B) administered corresponds to between about 0.02 mg/kg to about 100 mg/kg in the subject.

13. The pharmaceutical composition of claim 12, wherein the non-cyclic aliphatic group of Y comprises a secondary amine.

14. The pharmaceutical composition of claim 12, wherein the non-cyclic aliphatic group of Y comprises a tertiary amine.

15. The pharmaceutical composition of claim 12, wherein the central ring of the compound of Formula (1B) is unsaturated.

16. The pharmaceutical composition of claim 12, wherein the compound is

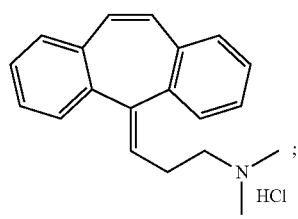

SW-01

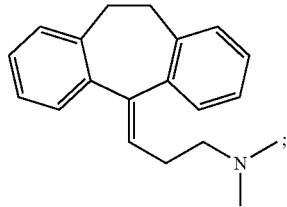

SW-05

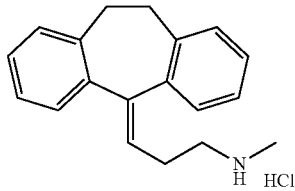

SW-02

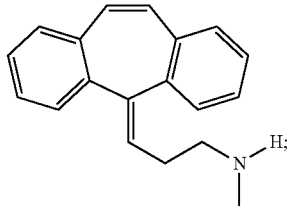

SW-15 or pharmaceutically acceptable salts thereof.

17. The pharmaceutical composition of claim 16, further comprising a pharmaceutically acceptable vehicle.

18. The pharmaceutical composition of claim 17, wherein the pharmaceutically acceptable vehicle is suitable for parenteral or intravenous administration.

19. The pharmaceutical composition of claim 12, further comprising a pharmaceutically acceptable vehicle.

20. The pharmaceutical composition of claim 19, wherein the pharmaceutically acceptable vehicle is suitable for parenteral or intravenous administration.

21. A method of suppressing tumour growth, proliferation, or both, associated with expression of RET gene, comprising administering a pharmaceutical composition as defined in claim 12 to a subject in need thereof.

22. The method of claim 21, wherein the tumour growth and/or proliferation is associated with a mutation of RET gene.

23. The method of claim 22, wherein said mutation produces a change of expression of RET gene or a change in RET kinase activity.

24. The method of claim 22, wherein said mutation is a chromosomal translocation.

25. The method of claim 22, wherein said mutation changes affinity of RET protein for ATP relative to wild type RET protein.

26. The method of claim 22, wherein said mutation is an activating mutation.

27. The method of claim 22, wherein said mutation is a point mutation.

28. The method of claim 22, wherein said mutation confers resistance to one or more of PP1, PP2, and vandetanib.

29. The method of claim 22, wherein said mutation is V804M or M918T.

30. The pharmaceutical composition of claim 12, wherein the tumour growth and/or proliferation is associated with a mutation of RET gene.

31. The pharmaceutical composition of claim 30, wherein said mutation produces a change of expression of RET gene or a change in RET kinase activity.

32. The pharmaceutical composition of claim 30, wherein said mutation is a chromosomal translocation.

33. The pharmaceutical composition of claim 30, wherein said mutation changes affinity of RET protein for ATP relative to wild type RET protein.

34. The pharmaceutical composition of claim 30, wherein said mutation is an activating mutation.

35. The pharmaceutical composition of claim 30, wherein said mutation is a point mutation.

36. The pharmaceutical composition of claim 30, wherein said mutation confers resistance to one or more of PP1, PP2, and vandetanib.

37. The pharmaceutical composition of claim 30, wherein said mutation is V804M or M918T.

38. The pharmaceutical composition of claim 12, wherein the amount of compound (1B) corresponds to between about 0.02 mg/kg to about 100 mg/kg in a patient in need thereof.

39. The pharmaceutical composition of claim 12, adapted for simultaneous co-administration of the compound (1B) and gemcitabine.

* * * * *